United States Patent
Stuart

(10) Patent No.: US 8,227,210 B2
(45) Date of Patent: Jul. 24, 2012

(54) POSITIVE CONTROL PROTEINS FOR GLUCOSE TRANSPORTER PROTEINS AND PROCESSES FOR THE GENERATION OF SUCH POSITIVE CONTROL PROTEINS

(75) Inventor: Charles A. Stuart, Johnson City, TN (US)

(73) Assignee: East Tennessee State University Research Foundation, Johnson City, TN (US)

( * ) Notice: Subject to any disclaimer, the term of this patent is extended or adjusted under 35 U.S.C. 154(b) by 0 days.

(21) Appl. No.: 12/635,973

(22) Filed: Dec. 11, 2009

(65) Prior Publication Data

US 2010/0173302 A1  Jul. 8, 2010

Related U.S. Application Data

(60) Provisional application No. 61/121,766, filed on Dec. 11, 2008.

(51) Int. Cl.
*C07K 14/00* (2006.01)
*C12Q 1/68* (2006.01)
(52) U.S. Cl. ..................... 435/69.1; 435/6.16
(58) Field of Classification Search ................. None
See application file for complete search history.

(56) References Cited

U.S. PATENT DOCUMENTS 6,346,390 B1 * 2/2002 Olsson et al. ............... 435/7.21
* cited by examiner

*Primary Examiner* — Tekchand Saidha
*Assistant Examiner* — Md. Younus Meah
(74) *Attorney, Agent, or Firm* — Luedeka Neely Group, P.C.

(57) ABSTRACT

Positive controls for experimentation related to membrane-bound glucose transporter proteins and methods for preparing such positive controls, such proteins including GLUT1, GLUT4, GLUT5, and GLUT12.

6 Claims, 14 Drawing Sheets

POSITIVE CONTROL PROTEINS FOR GLUCOSE TRANSPORTER PROTEINS AND PROCESSES FOR THE GENERATION OF SUCH POSITIVE CONTROL PROTEINS

CROSS-REFERENCE(S) TO RELATED APPLICATION(S)

This patent application is a U.S. nonprovisional application which claims priority to U.S. Provisional Application Ser. No. 61/121,766 filed on. Dec. 11, 2008, entitled POSITIVE CONTROL PROTEINS FOR GLUCOSE TRANSPORTER PROTEINS AND PROCESSES FOR THE GENERATION OF SUCH POSITIVE CONTROL PROTEINS to Charles A. Stuart, the content of which is incorporated herein by reference in its entirety.

STATEMENT REGARDING NOTICE OF COPYRIGHT

A portion of the disclosure of this patent document contains material that is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE DISCLOSURE

This disclosure relates to the field of positive control proteins for use during experimentation of various proteins.

BACKGROUND

Immunoblotting or "Western" blotting technology has been developed to detect specific proteins in a specimen. Western blotting typically includes at least four primary steps including protein separation, protein transfer, membrane blocking, and protein detection. In immunoblotting gel electrophoresis is used to separate native or denatured proteins. For example, one mode of separation using gel electrophoresis separates proteins based on molecular weight. Persons having ordinary skill in the art are aware of the various ways gel electrophoresis may be used to separate proteins, so these variations will not be discussed in detail here.

After protein separation in a western blotting procedure, the separated proteins are typically transferred to a membrane using techniques known to person having ordinary skill in the art. Other steps such as "blocking" may be necessary to ensure that only certain proteins react with the transfer membrane which, in turn, better ensures that detection information is more accurate. The detection step includes probing the membrane for a particular protein of interest using a modified antibody. When the protein of interest is detected by the modified antibody, a reaction takes place that may be used to generate a visual indication. The magnitude of the visual indication corresponds to the amount of protein present. The location of the visual indication in the gel corresponds, for example, to the molecular weight of the protein.

In all experiments using some form of the scientific method, a control group is necessary to verify and/or frame the results obtained with regard to an experimental group. In the case of western blotting, a sample containing unknown proteins is used as the experimental group while samples of known purified proteins are used as the control group to compare to results from the experimental group. In order for a protein to be used as a positive control, however, it must be water soluble and highly purified or the experiment will necessarily have a greater potential of leading to less accurate conclusions.

A positive control is available for many classes of proteins, but no positive control is currently available for any of the membrane-bound glucose transporter proteins such as, for example, SEQ ID NO. 10 (GLUT1), SEQ ID NO. 12 (GLUT4), SEQ ID NO. 13 (GLUT5), and SEQ ID NO. 16 (GLUT12). This is true because all of these proteins are very hydrophobic and are very difficult to purify.

What is needed, therefore, are positive controls for membrane-bound glucose transporter proteins and a method for preparing such positive controls.

SUMMARY

The above and other needs are met by a class of ovalbumin-chimeric proteins that can accurately operate as positive controls for membrane-bound glucose transporter proteins. More specifically, ovalbumin is a readily available protein that is highly water soluble and easily purified. An ovalbumin-like protein may be created using bacteria in which some of the codons of the ovalbumin coding region are replaced with sequence encoding, for example, the twelve amino acids of a specific glucose transporter protein (e.g., SEQ ID NO. 10 (GLUT1)). By replacing the end of the ovalbumin with important identifiable amino acids of a known glucose transporter protein, a new overall protein is created that includes a known mass of ovalbumin and a known mass of a specific glucose transporter protein, wherein the new protein is highly soluble and may be easily purified. There are many antibodies available that may be used in western blotting that bind to glucose transporter proteins, so when an ovalbumin chimeric protein is located in a gel and a proper antibody is applied thereto, the antibody is effectively "tricked" such that it appears as if a chain of an entire glucose transport protein were present. Thus, because the overall molecular weight of a particular chimeric protein is known, ovalbumin-chimeric proteins may be produced that may effectively be used as positive controls for glucose transporter proteins.

In a preferred embodiment, a particular ovalbumin-chimeric protein is created from ovalbumin and SEQ ID NO. 10 (GLUT1). In a related embodiment, a particular ovalbumin-chimeric protein is created from ovalbumin and SEQ ID NO. 12 (GLUT4). In another embodiment, a particular ovalbumin-chimeric protein is created from ovalbumin and SEQ ID NO. 13 (GLUT5). In yet another embodiment, a particular ovalbumin-chimeric protein is created from ovalbumin and SEQ ID NO. 16 (GLUT12)

The commercial utility of the ovalbumin-chimeric protein standards is as follows with SEQ ID NO. 12 (GLUT4) as an example.

1. The SEQ ID NO. 12 (GLUT4) will serve as a positive control in western blotting when it is used with any of these commercially available antibodies:
   a. AB65976 from AbCam
   b. GT41-A from Alpha Diagnostics International
   c. AB 1049 from Chemicon
   d. AB1346 from Millipore There are several similar antibodies available for the C-terminus of human SEQ ID NO. 12 (GLUT4) from other companies. Each is marketed in an aliquot that typically can be used in 20-50 assays and retails thr $275-$300. These antibodies are virtually always marketed together with an aliquot of the immunizing peptide that is used to establish non-specific labeling with the antibody. This aliquot is enough for 2-10 assays and is usually sold for about $100. A positive control is available for some classes of protein antigens, but is not available for any of the membrane-bound glucose transporter proteins.

2. Each aliquot of SEQ ID NO. 12 (GLUT4) contains a known concentration of the protein in femtomoles/10 uL for quantitative comparison with proteins of unknown concentration run on the same gel. Using these reagents, we have shown that normal human muscle contains about 2 femtomoles of the insulin-responsive glucose transporter protein (SEQ ID NO. 12 (GLUT4)) in 20 μg of total protein from homogenized skeletal muscle. Further, with the additional standards SEQ ID NO. 10 (GLUT1), SEQ ID NO. 24 (GLUT5), and ova-GLUT12, we have quantified for the first time anywhere the actual amounts of GLUT1, SEQ ID NO. 12 (GLUT4), SEQ ID NO. 13 (GLUT5), and SEQ ID NO. 16 (GLUT12) proteins that are present in normal muscle (see manuscript "exereise_bike_draft_27_with_small_figures").

3. The relative mobility of SEQ ID NO. 12 (GLUT4) is 41 kDa on polyacrylamide gel electrophoresis. This gives it a predictable relative position in the gel that is close to the usual position of the native SEQ ID NO. 12 (GLUT4) at about 45 kDa.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several view, and wherein:

DETAILED DESCRIPTION

Figure 1:
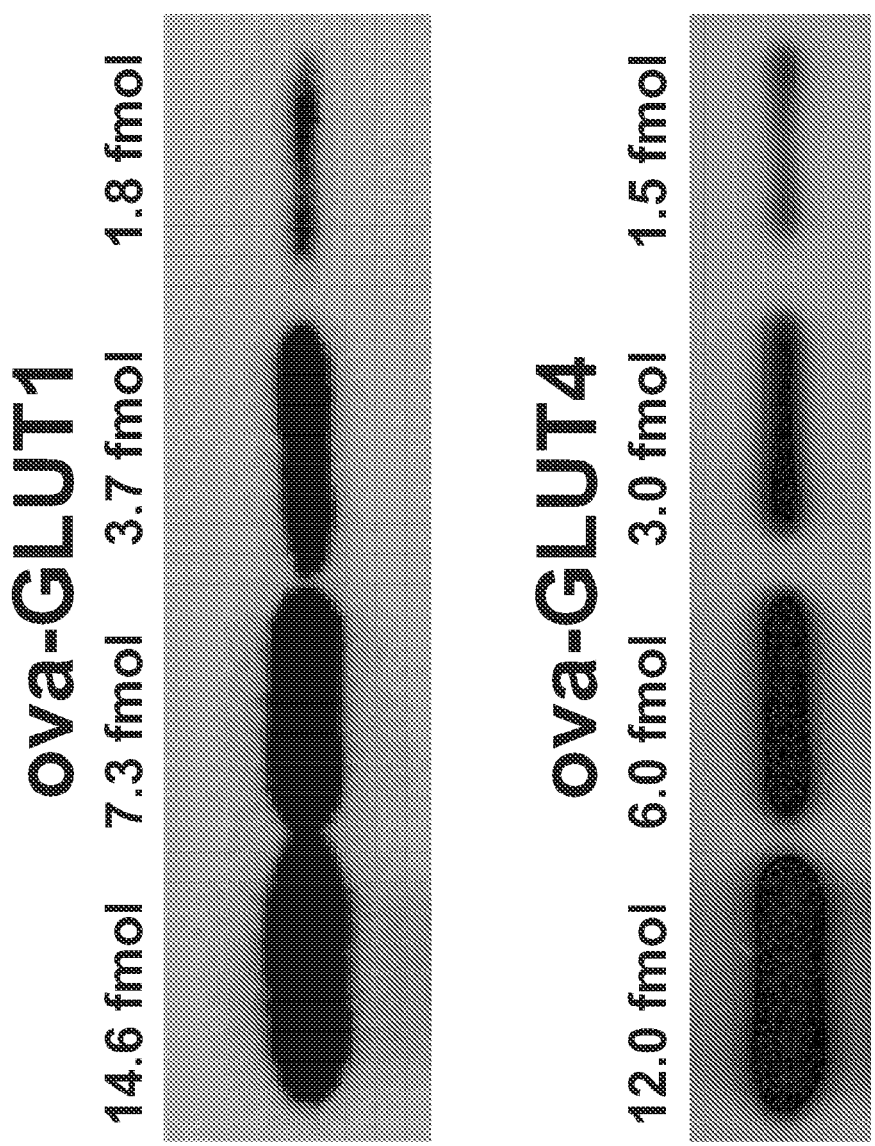
FIG. 1 shows a schematic view of serial dilutions of ova-GLUT1 and ova-GLUT4 on immunoblots.

The following description of preferred embodiments for the present disclosure has been presented for purposes of illustration and description. The embodiments are not intended to be exhaustive or to limit the invention to the precise form disclosed. Obvious modifications or variations are possible in light of the teachings herein. The embodiments are chosen and described in an effort to provide illustrations of the principles of the invention and its practical application, and to thereby enable one of ordinary skill in the art to utilize the invention in various embodiments and with various modifications as are suited to the particular use(s) contemplated. All such modifications and variations are within the scope of the invention as determined by the appended claims when interpreted in accordance with the breadth to which they are fairly, legally, and equitably entitled.

Introductory Remarks

To determine if resistance training of sedentary subjects would increase the expression of the principle muscle glucose transporters, six volunteers completed six weeks of progressively increasing intensity stationary cycle cycling. In vastus lateralis muscle biopsies, SEQ ID NO. 10 (GLUT1), SEQ ID NO. 12 (GLUT4), SEQ ID NO. 24 (GLUT5), and SEQ ID NO. 16 (GLUT12) were compared using quantitative immunoblots with specific protein standards. SEQ ID NO. 10 (GLUT1) was unchanged, SEQ ID NO. 12 SEQ ID NO. 12 (GLUT4) increased 66%, SEQ ID NO. 16 (GLUT12) increased 104%, and SEQ ID NO. 24 (GLUT5) decreased 72%, A mitochondrial marker (cytochrome c) and regulators of mitochondrial biogenesis (PGC-1a and phospho-AMPK) were unchanged, but the muscle hypertrophy pathway component, phospho-mTOR increased 83% after the exercise program. In baseline biopsies, SEQ ID NO. 12 (GLUT4) by immunohistochemical techniques was 37% greater in type I (slow twitch, red) muscle fibers, but the exercise training increased SEQ ID NO. 12 (GLUT4) expression in type II (fast twitch, white) fibers by 50%, achieving parity with the type I fibers. Baseline phospho-mTOR expression was 50% higher in type II fibers and increased more in type II fibers (62%) with training, but also increased in type I fibers (34%). We conclude that progressive intensity stationary cycle training of previously sedentary subjects increased muscle insulin-responsive glucose transporters (SEQ ID NO. 12 (GLUT4) and GLUT12) and decreased the fructose transporter (SEQ ID NO. 24 (GLUT5)).

The increase in SEQ ID NO. 12 (GLUT4) occurred primarily in type II muscle fibers and this coincided with activation of the mTOR muscle hypertrophy pathway. There was little impact on type I fiber SEQ ID NO. 12 (GLUT4) expression and no evidence of change in mitochondrial biogenesis.

Introduction

Exercise is one of the cornerstones of prevention and treatment of diabetes. Exercise training has been shown to improve insulin resistance and to improve blood sugar control in patients with type 2 diabetes (10; 29; 54). Both aerobic training and strength training are beneficial, even though their effects are apparently brought about via separate pathways in muscle (5).

The muscle response to exercise training is dramatically different depending on whether the program is for endurance or for strength (5; 40). Not only is the muscle histological response different but the intracellular signaling pathways are discrete (32). Endurance training causes type I muscle fibers (slow twitch, red fibers) to substantially increase their mitochondrial content and thus increase the oxidative capacity and enhance the efficiency of energy generation from fuel (fatty acids and glucose) (5). In contrast, strength training can result in substantial skeletal muscle fiber hypertrophy. The increased cross-sectional area involves primarily Type II fibers (fast twitch, white) leads to increased maximum strength (8). Strength training normally affects both muscle fiber types but for some reason (that is not completely understood) Type II fibers tend to hypertrophy at a faster rate (2; 19) Muscle fiber hypertrophy is energy intensive and involves the net increase in muscle contractile apparatus via increased protein synthesis and decreased degradation (7).

Classic studies of one leg endurance training conclusively demonstrated that 5'-AMPactivated protein kinase (AMPK) is increased in amount and activation by a single bout of aerobic exercise and by endurance training (18). Additional studies have shown that aerobic exercise of long duration results in a rise in the AMP:ATP ratio which allows an upstream kinase, LKB1 to activate AMPK. AMPK and calmodulin-activated protein kinase (CamK) phosphorylate histone deacetylases (HDAC), allowing myocyte-enhancing factor 2 (MEF2) to bind to the promoter of peroxisome proliferator activating receptor γ coactivator 1a (PGC-1a). PGC-1a coregulates the expression of respiratory genes, mitochondrial transcription factor A (MTF-A), fatty acid oxidation enzymes, SEQ ID NO. 12 (GLUT4), and slow myosin heavy chain (43).

Resistance training activates an entirely different signaling pathway. Net increase in muscle protein synthesis appears to involve a muscle protein kinase called mammalian target of rapamycin (mTOR). There are a complex series of upstream and downstream steps that involve PDKI-mediated phosphorylation of mTOR that is part of a protein complex (TORO 1) which in turn phosphorylates 70 kDa S6 protein kinase (S6K1) and 4E binding proteins (4E-BP), both involved in growth-related protein synthesis (5; 7). Eukaryotic initiation factor 2 (eIF2), a regulator of general protein synthesis, is activated in parallel to mTOR via PDKI phosphorylation of PKB which phosphorylates and inactivates glycogen synthase kinase (GSK3β) releasing inhibition of eIF2 (5). Animal studies suggest that mTOR is necessary for muscle growth or hypertrophy, but is not needed for maintenance of muscle size in adult animals (7). There is some evidence that activation of the AMPK/PGC-1α pathways by endurance training may suppress the muscle hypertrophy effects of the mTOR pathways (32; 39). To our knowledge a study combining features of both strength and endurance training has not been previously performed.

In the current study, sedentary subjects volunteered for six weeks of supervised exercise training on stationary cycles. The exercise program was designed to increase the strength of the quadriceps muscles as well as to increase the endurance of the subjects. Changes in the principle glucose transporters in vastus lateralis were quantified. In addition, changes in mitochondrial biogenesis and its principle regulator were measured, as well as a key member of the muscle hypertrophy pathway. This exercise program caused a significant increase in thigh muscle SEQ ID NO. 12 (GLUT4) and SEQ ID NO. 16 (GLUT12), and a decrease in SEQ ID NO. 24 (GLUT5). The increase in SEQ ID NO. 12 (GLUT4) occurred primarily in type II fibers and was coincident with a substantial increase in phospho-mTOR in the same fibers.

Methods

Protocol and subject selection: Eight sedentary normal subjects were recruited to undergo six weeks of supervised exercise training. The research protocol and the written consent documents were approved by the East Tennessee State University Institutional Review Board. Subjects were otherwise well except that they were not engaged in any regular organized or planned exercise. Six subjects, whose characteristics are shown in Table 1, successfully completed the training and the planned measurements. The exercise program was performed at the ETSU Exercise and Sports Sciences Laboratory with students from Kinesiology in constant attendance under the supervision of Dr. Diego de Hoyos. While strength versus endurance training has been shown to produce relatively specific responses (5; 40). However, a combination of strength and endurance training may produce different effects compared to strength or endurance training alone. In the present study a "combination" training program was purposely selected as the effects have not been previously studied. Thus the training program was designed to incorporate features of both resistance exercise and endurance exercise. The training program consisted of one hour three times per week. Initially, five minutes of low revolutions<50 rpm) was alternated with ten minutes of 60-75 rpm at the lowest intensity setting. Each week the intensity setting on the cycle was increased, such that at the end of six weeks the subjects were achieving higher intensity cycling intervals with a targeted sustained heart rate of 85% of maximal. Body composition, $VO_2$max, plasma insulin, and plasma glucose concentrations were measured prior to and at the end of tae training. Quantification of lean mass and fat mass was performed by dual energy x-ray absorptiometry (DEXA) using a Hologic QDR 1000/w (Waltham. MA). An indirect calorimeter (Sensormedics 2400 Metabolic Measurement System—Yorba Linda, Calif.) was used with a treadmill to determine $VO_2$max.

Materials: Affinity-purified rabbit antibodies against h-SEQ ID NO. 10 (GLUT1) and h SEQ ID NO. 24 (GLUT5) were purchased from Alpha. Diagnostics (San Antonio, Tex.). SEQ ID NO. 12 (GLUT4) antibodies (AB 1049, goat anti-human) were purchased from Chemicon (Temecula, Calif.). Rabbit anti-h SEQ ID NO. 16 (GLUT12) antibodies (RDI SEQ ID NO. 16 (GLUT12)abrx) were purchased from Research Diagnostics (Flanders, N.J.). Rabbit anti-PGC-1a antibody was purchased from Chemicon (AB3242). Rabbit antibodies for phospho-AMPKα1 (#2531) and phosphomTOR (#2971) were purchased from Cell Signaling Technology (Danvers, Mass.). Goat antibodies against actin were purchased from Santa Cruz Biotechnology (sc-1616) and sheep anti-cytochrome c antibodies (AB3547) were purchased from Chemicon. Mouse monoclonal antibody against fast myosin (GTX73432) was purchased from GeneTex (San Antonio, Tex.). All other chemicals were reagent grade.

Muscle biopsies: Percutaneous needle biopsies of the vastus lateralis were performed after an overnight fast and two hours of quiet recumbency as previously described (50). Briefly, after local lidocaine anesthesia, a 7-10 mm skin incision was made and a Bergstrom-Stille 5 mm muscle biopsy is introduced through the fascia, and under suction, a 50-100 mg specimen is obtained. After quickly blotting, the entire sample was frozen in liquid nitrogen for later analysis. Muscle homogenate was prepared by placing 25-50 mg muscle in 500 µL 0.25 M sucrose, 20 HEPES, pH 7.4, containing protease inhibitors (Halt Protease Inhibitor Cocktail Kit from Pierce), and homogenizing with two 30 second bursts of a hand-help homogenizer (Pellet Pestle Motor from Kontes).

Quantification of SEQ ID NO. 12 (GLUT4) mRNA: Total RNA was isolated from 25-50 mg of muscle using the RNeasy Mini Kit and subjected to on-column DNase treatment according to the manufacturer's protocol (Qiagen, Valencia, Calif.). RNA quality was analyzed using an Agilent 2100e Bioanalyzer (Agilent Technologies, Santa Clara, Calif.) and only samples with an RNA Integrity Number (RIN) of 7.0 or above was used in subsequent experiments cDNA was generated by reverse transcription of 300 ng total RNA with oligo dT primers using the GeneAmp RNA PCR Core Kit (Applied Biosystems, Foster City, Calif.). Quantitative real-time PCR of SEQ ID NO. 12 (GLUT4) mRNA was performed on a Bio-Rad iCycler (Hercules, Calif.) using primers and detection conditions as previously described (50). All samples were amplified in triplicate from three separate biologic replicates. GAPDH mRNA was quantified from each sample as previously described (59) and used as a reference transcript.

PCR was carried out using Accuprime DNA polymerase from Invitrogen. After 2 minutes of denaturing the DNA template at 94° C., the template was amplified by 35 cycles of 94° C. for 15 seconds, 56° C. for 30 seconds, and 72° C. for 75 seconds. Reaction products were then extended for 9 minutes at 72° C.

Glucose transporter protein standards: The construct SEQ ID NO. 1 was generated to express a soluble chimeric protein comprised of ovalbumin and a SEQ ID NO. 10 (GLUT1) epitope tag. Chicken ovalbumin (nt 66-68, 81-1223; Genbank accession V00383) was amplified from SEQ ID NO. 29 (generously provided by Dr. Michel Sanders of the University of Minnesota) using the primers SEQ ID NO. 19 and SEQ ID NO. 20 (Table 2) and TA-cloned into pCR T7 TOPO (Invitrogen, Carlsbad, Calif.). As the ovalbumin coding region in SEQ ID NO. 29 was incomplete, missing the first five codons and first by of the sixth codon, a sense primer (ova Fl) was designed to restore the initiator ATG and correct the sixth codon, while excluding the second through fifth codons. The antisense primer (SEQ ID NO. 20) was complimentary to ovalbumin nt 1201-1222 and included sequence encoding the C-terminal 12 amino acids of human SEQ ID NO. 10 (GLUT1) (aa 481-492; SwissProt accession PI1166). Codons were optimized for *E. coli* usage. Chimeric protein was expressed using a coupled in vitro transcription/translation system (Active Pro In Vitro Translation kit, Ambion, Inc.) according to the manufacturer's protoco\' The amount of chimeric protein generated was then quantified using the Agilent Bioanalyzer 2100e. The ova-SEQ ID NO. 10 (GLUT1) fusion protein had a deduced molecular weight of 44,244 daltons and migrated as a discrete band, which represented 3.5% of the total protein present. Further purification was not necessary when the product was used as a standard in gel electrophoresis and immunoblotting.

The chimeric constructs used in this study (SEQ ID NO. 3, SEQ ID NO. 4 SEQ ID NO. 7) as well as those for SEQ ID NO, 11, mGlut3 SEQ ID NO. 14 and SEQ ID NO. 15 were generated using the same protocol as for SEQ ID NO. 10 (GLUT1), with the exception that the anti-sense primer was changed to correspond to the appropriate GLUT carboxy terminus sequence (Table 2). FIG. 1 displays Immunoblots of serial dilutions of SEQ ID NO. 10 (GLUT1) and SEQ ID NO. 12 (GLUT4).

Immunoblots: The techniques used for performing immunoblots were described previously (49; SO). Quantitative immunoblots were performed for SEQ NO. 12 (GLUT4), SEQ ID NO. 24 (GLUT5), and SEQ ID NO. 16 (GLUT12) using image analysis (Quantity One version 4.5.2, BioRad) of blots that included known amounts of the corresponding ovalbumin-antigen chimeric protein.

Immunohistochemistry: Confocal microscopic assessments of specific fluorescent labeling of phospho-mTOR protein in human muscle sections were performed using methods previously described for glucose transporters (SO). Muscle fiber type composition was determined using an anti-fast myosin heavy chain monoclonal antibody and methods previously described (SO). Muscle fiber type-specific protein expression was quantified as previously described (49). Briefly, all sections were digitized, coded, and then signal intensity was quantified using Quantity One software by an investigator who was unaware of which subject or treatment each of the images represented.

Muscle fiber size cross-sectional area: Frozen muscle specimens were cut perpendicular to the fiber direction using a Leica CM3050 S cryostat and pre-training and post-training sections were placed on the same slide in the same order for each subject. Sections were evaluated for fiber cross-sectional area determination after they were treated with a fluorescent antibody that distinguished between type I and type II fibers. Digital images were obtained that included a key of a known dimension which were coded and submitted to the technician for quantification. In each image, ten type I fibers and ten type II fibers had their two major diameters measured (d1 and d2) and the area estimated by the formula for an ellipse ($\pi$'d$_1$/2'd$_2$/2). Statistics: All data are displayed as mean±standard error. Paired t test was used for comparisons before and after training. Effect size correlations were calculated using Cohen's d (22). Statistical procedures were performed using SigmaStat version 3.11 from Systat Software (San Jose, Calif.

Results

Effects of six weeks of stationary cycle training on muscle expression of glucose transporters SEQ ID NO. 10 (GLUT1), SEQ ID NO. 12 (GLUT4), SEQ ID NO. 24 (GLUT5), and SEQ ID NO. 16 (GLUT12): Eight previously sedentary subjects volunteered to undergo six weeks of training on a stationary cycle, and six completed the protocol. The subject characteristics are shown in Table 1. Two subjects were obese (BMI>30), three were overweight (BMI 25 to 30), and one was normal in weight. All subjects had normal fasting plasma glucose concentrations and there was no diabetes in parents or siblings. The training was individually supervised by students in the Kinesiology, Leisure, and Sports Science Department acting as a "personal trainers". Training sessions were one hour periods three times per week, each with alternating intervals of low rpm (five minutes) and high rpm (ten minutes). The intensity of the training was increased each week by increasing the resistance setting on the cycle, beginning with three ten minute intervals alight intensity until the subjects were able to sustain moderate intensity cycling for the three ten minute exercise intervals. Table 3 displays the pre- and post-training $VO_2$max, body composition, and fasting glucose and insulin data. Body composition, fasting glucose and insulin concentrations were not changed by the training program. Body mass index appears to have increased slightly with a "p value" of 0.031 by paired t-test. However, the effect size was quite small indicating little training effect on. BMI. The small change in $VO_2$max did not achieve statistical significance because the data failed the normality test and significance was tested using the Wilcoxon Signed Rank Test, However, an effect size of 0.56 suggests a moderate positive training effect on a measure of cardio-respiratory related endurance. It is possible that significance would have been reached had a more mechanically specific cycle max $VO_2$ tests had been used, However, the necessary cycle ergometer equipment was not available.

Figure 2:
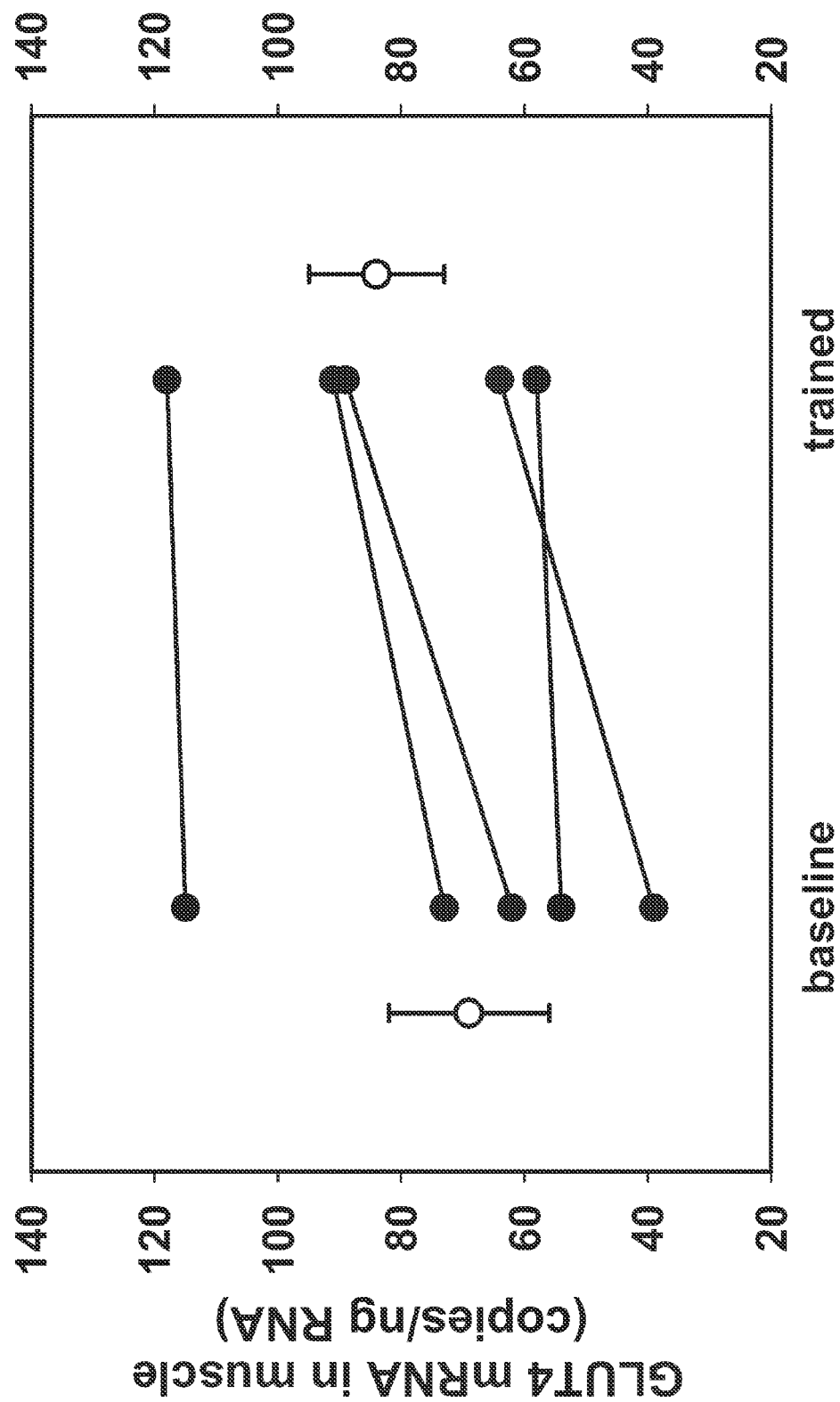
FIG. 2 shows a schematic graphical view of GLUT4 mRNA in muscle (copies/ng RNA) versus a progression from baseline to trained state.
Figure 3:
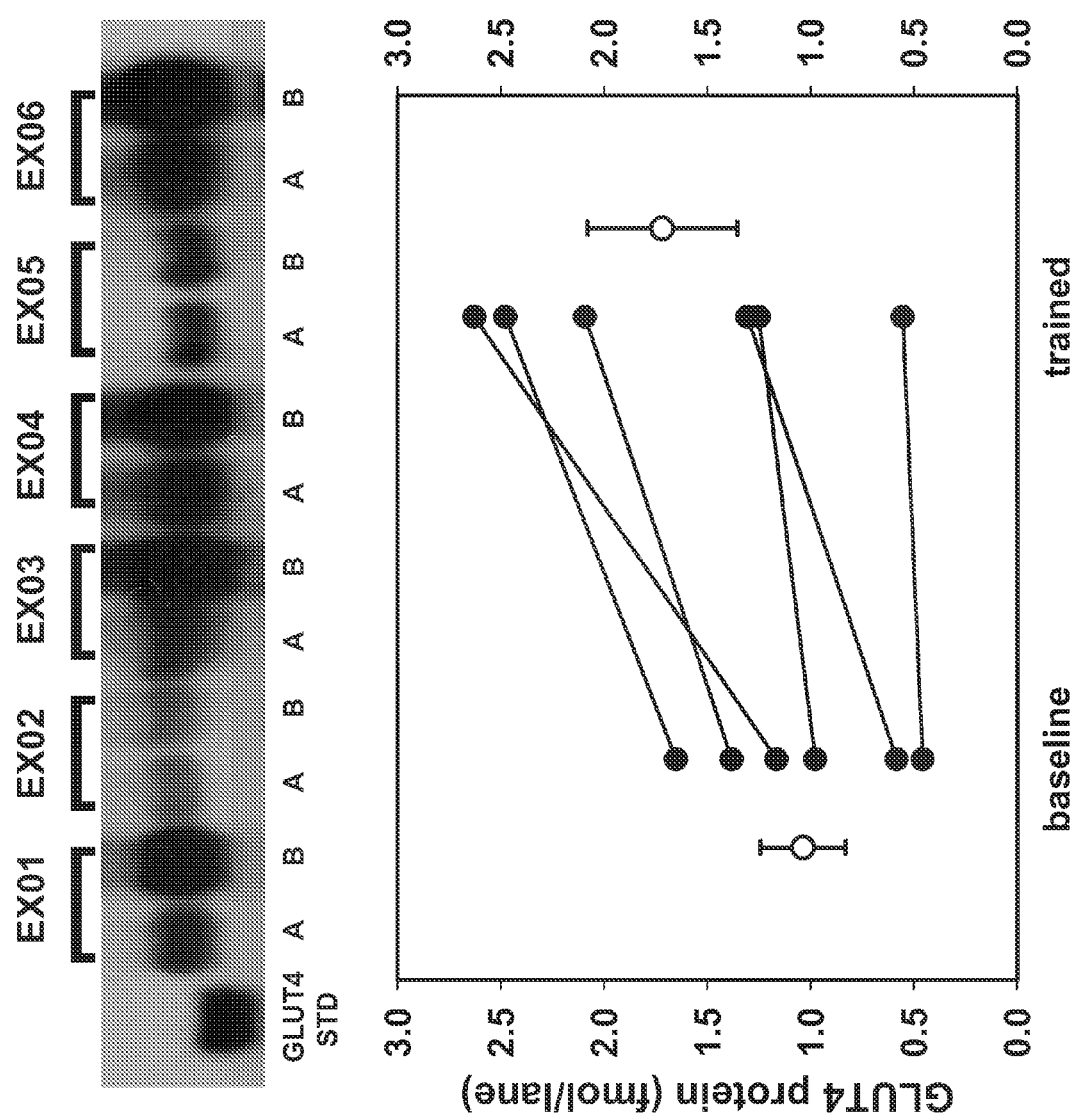
FIG. 3 shows a schematic graphical view of GLUT4 protein (fm ol/lane) versus a progression from baseline to trained state.
Figure 4:
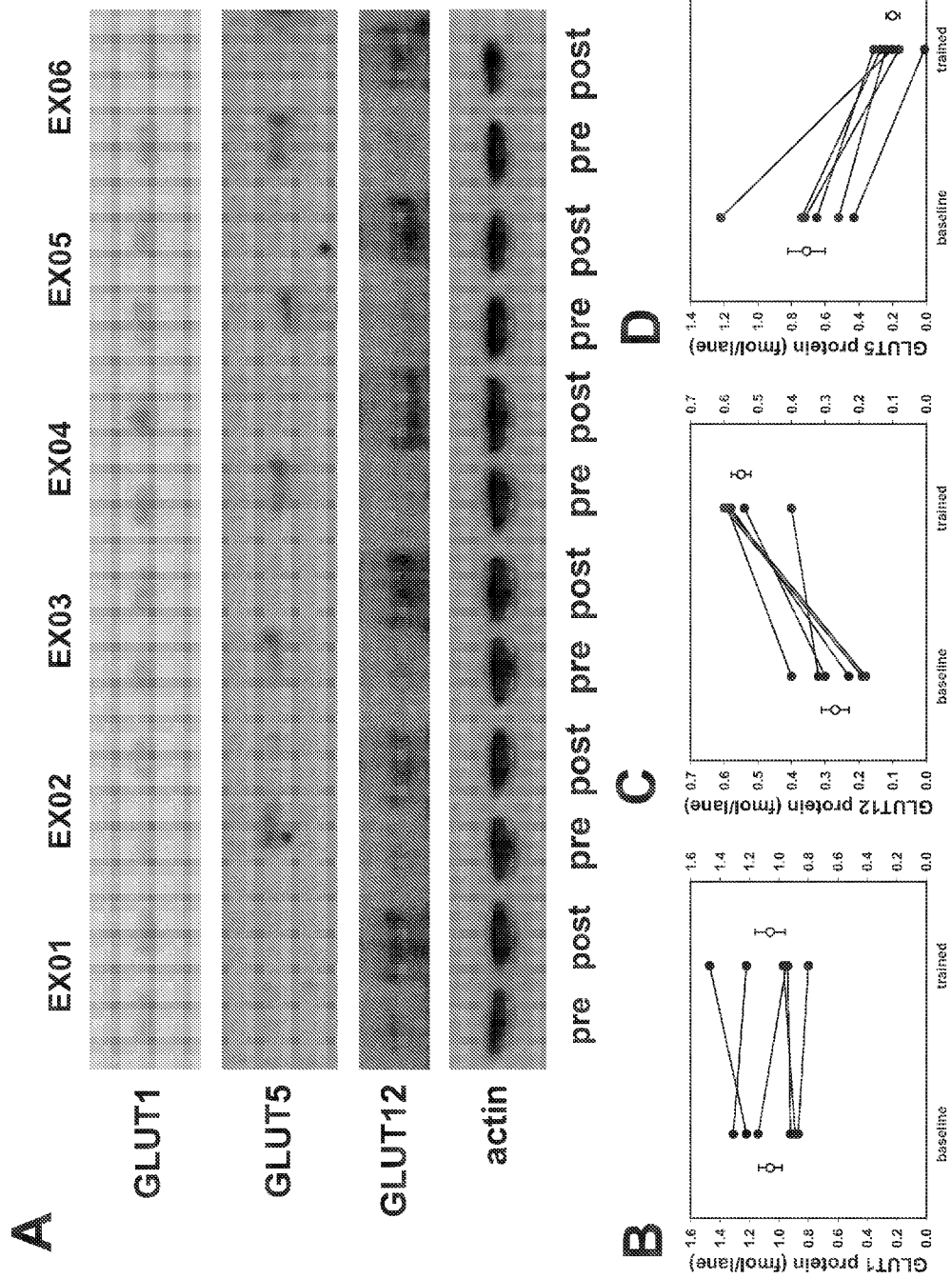
FIG. 4A shows a schematic view of changes in GLUT5 and GLUT12 induced by six weeks of stationary cycle training.
FIG. 4B shows a schematic graphical view of changes in GLUT1 included by six weeks of stationary cycle training.
FIG. 4C shows a schematic graphical view of changes in GLUT12 induced by six weeks of stationary cycle training.
FIG. 4D shows a schematic graphical view of changes in GLUT5 induced by six weeks of stationary cycle training.

Percutaneous biopsies of the vastus lateralis were performed in the week prior to commencement of training and repeated from the contralateral leg 40-48 hours after the last exercise session. Both SEQ ID NO. 12 (GLUT4) mRNA and protein increased significantly (22% and 66%, respectively) as shown in FIGS. 2 and 3. FIG. 4 shows the immunoblots for SEQ ID NO. 10 (Guar), SEQ ID NO. 24 (GLUT5) and SEQ ID NC). 16 (GLUT12). SEQ ID NO. 10 (GLUT1) did not change, but SEQ ID NO. 16 (GLUT12) from muscle homogenate increased 104% and SEQ ID NO. 24 (GLUT5) declined 72%. The mean data from quantification of each of the four principle muscle GLUT's are displayed in FIG. 5. SEQ ID NO. 12 (GLUT4) represented half of hexose transporters in the baseline muscle biopsies and demonstrated the largest absolute training-related increment in transporters, making up 65% of the glucose transporters in the trained muscle. These data suggest that the 0.5 fmol/20~g decline in the fructose transporter, SEQ ID NO. 24 (GLUT5) was more than offset by increased SEQ ID NO. 12 (GLUT4) and SEQ ID NO. 16 (GLUT12), totaling 1.6 fmol/20 µg.

Figure 6:
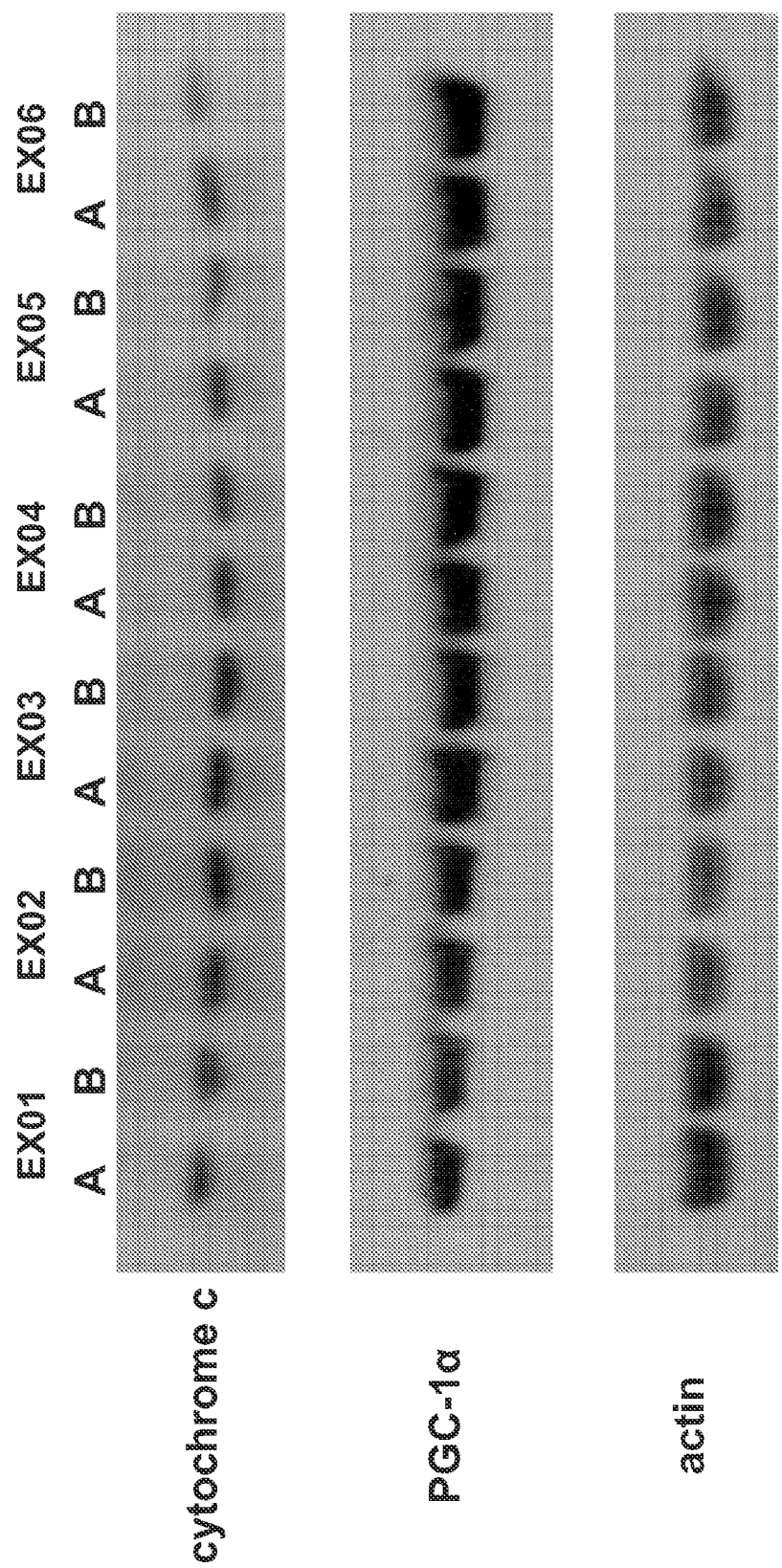
FIG. 6 shows a schematic view of changes in cytochrome c and PGC-1α by an exercise training program.

Effects of six weeks of stationary cycle training on muscle expression of cytochrome c and PGC-1a: Mitochondrial expression should be increased if the training sessions described above were primarily aerobic. We therefore quantified changes in a mitochondrial marker, cytochrome c. Immunoblots of the six subjects' homogenates from pre- and post-training muscle biopsies were quantified by image analysis. FIG. 6 displays a typical cytochrome c immunoblot. There was a mean 6% decrease that was not statistically significant. Peroxisome proliferator-activated receptor-γ coactivator-1α. (pGC-1α) is the principle regulator of mitochondrial biogenesis (4; 43).

We, therefore, quantified changes in its expression in the muscle biopsies from this study. FIG. 6 also displays a representative PGC-1α. immunoblot. PGC-1α. expression was not significantly altered by the training program.

Figure 7:
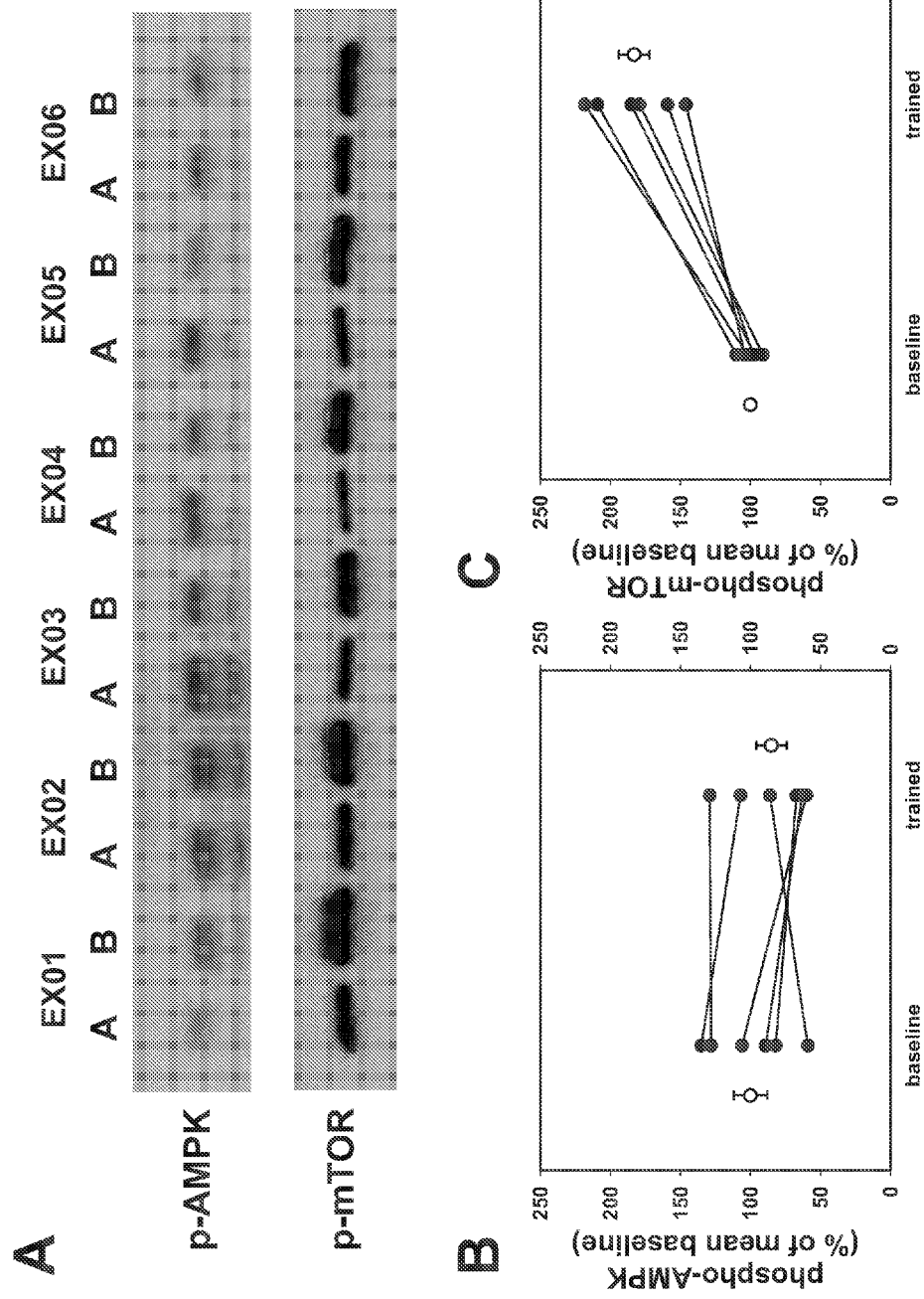
FIG. 7A shows a schematic view of changes in phosphor-AMPK and phosphor-mTOR induced by six weeks of cycle training of sedentary volunteers.
FIG. 7B shows a schematic graphical view of changes in phosphor-AMPK induced by six weeks of cycle training of sedentary volunteers.
FIG. 7C shows a schematic graphical view of changes in phosphor-mTOR induced by six weeks of cycle training of sedentary volunteers.

Effects of six weeks of stationary cycle training on muscle expression of phospho-AMPK and phospho-mTOR: Since endurance training exercise causes muscle adaptation primarily through stimulation of AMP-kinase (AMPK) phosphorylation (36), we quantified the change in phospho-AMPK in immunoblots as shown in FIG. 7. Conversely, strength training exercise exerts its effects via a separate and distinct pathway that involves phosphorylation of mammalian target of rapamycin (mTOR) (5; 7). We also quantified phospho-mTOR in immunoblots as shown in FIG. 7, Panels A and C. The exercise training program that we employed resulted in a near doubling of the phospho-mTOR and a 12% decrease in phospho-AMPK that was not statistically significant. These data suggest that the stationary cycle training program did not produce typical aerobic training effects but was more characteristic of strength training effects for the quadriceps muscles that were biopsied.

Figure 8:
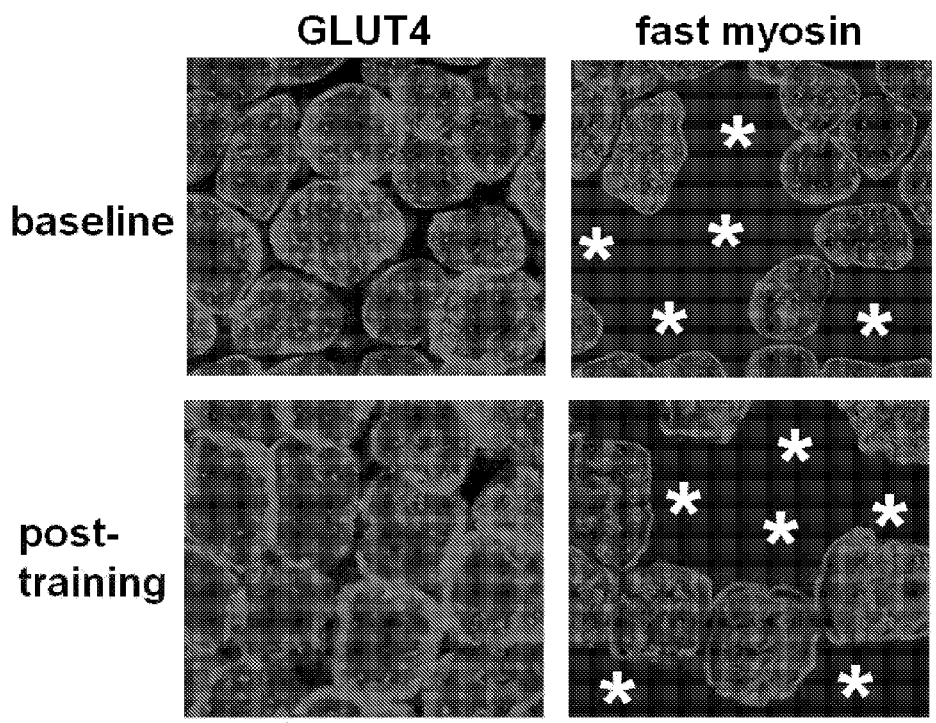
FIG. 8A shows a schematic view of muscle fiber-specific changes in GLUT4 induced by six weeks of cycle training.
FIG. 8B shows schematical graphical views of Type I and Type II muscle fiber changes, respectively, in GLUT4 induced by six weeks of cycle training.
Figure 8:
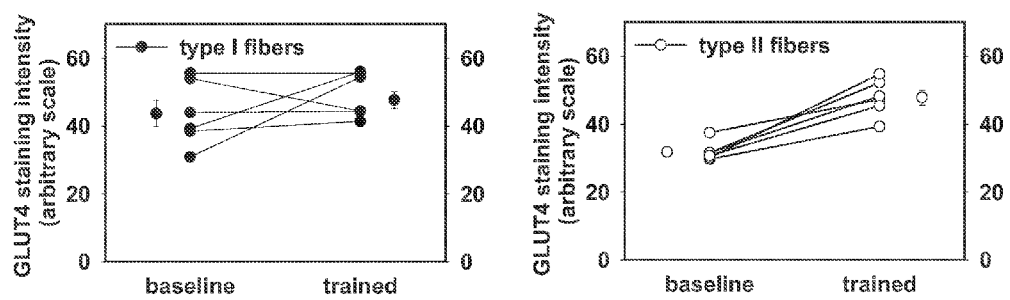

Muscle fiber type and the changes in SEQ ID NO. 12 (GLUT4) expression: SEQ ID NO. 12 (GLUT4) is expressed predominantly in type I muscle fibers with the ratio of SEQ ID NO. 12 (GLUT4) in type I to its expression in type II fibers approaching 3 to 1 in some reports (20; 50), whereas SEQ ID NO. 24 (GLUT5) and mTOR are expressed at higher concentrations in type II fibers (7; 49; 50). Since strength training usually results in changes primarily in type II fibers, we evaluated by immunohistochemistry which fiber accounted for the bulk of the increase in SEQ ID NO. 12 (GLUT4) that we documented by immunoblotting of muscle homogenates. To accurately compare the expression of SEQ ID NO. 12 (GLUT4) in the pre-training and post-training biopsy material, the two specimens from each subject were cut and mounted at the same time on the same glass slide. The pre- and post-training samples were then probed together simultaneously in a single incubation on that slide. Images of each slide were made with the same magnification and settings of the confocal microscope so that image analysis program settings were also identical and directly comparable. FIG. 8 shows the results of these studies. Panel A displays one subject's images that manifest an exercise training-related reversal of the SEQ ID NO. 12 (GLUT4) fiber type dominance. The baseline sample image shows SEQ ID NO. 12 (GLUT4) expressed at higher levels in the type I fibers, whereas the post-training image shows SEQ ID NO. 12 (GLUT4) actually expressed at higher concentrations in the type II fibers. Panel B displays the individual image analysis generated SEQ ID NO. 12 (GLUT4) signal intensity data for all six subjects. In baseline samples, type I fibers expressed 37% more SEQ ID NO. 12 (GLUT4) than did type II fibers. After exercise training, type II fiber SEQ ID NO. 12 (GLUT4) increased by 50% (p=O.OO1) above type II baseline, whereas the 9% SEQ ID NO. 12 (GLUT4) increase in type I fibers was not statistically significant (p=0.510). The post-training SEQ ID NO. 12 (GLUT4) signal intensity in type II fibers was 101% of that in type I muscle fibers.

Figure 9:
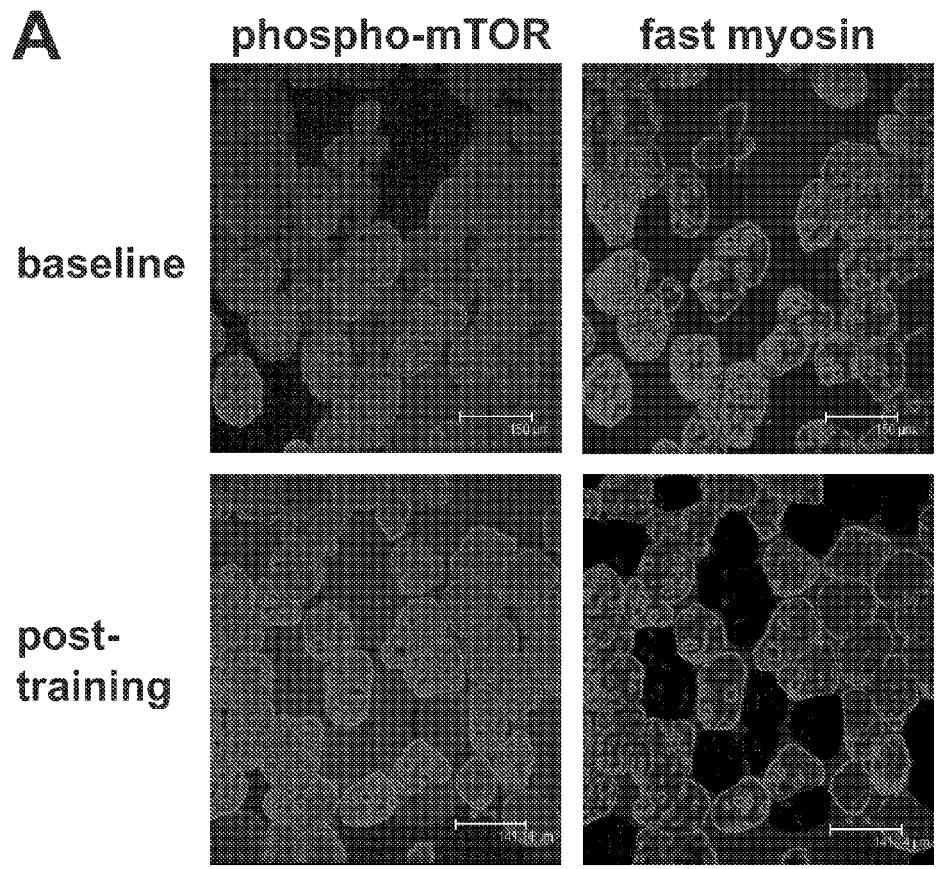
FIG. 9A shows a schematic view of muscle fiber-specific changes in phosphor-mTOR from cycle training.
FIG. 9B shows a schematic graphical view of muscle fiber-specific changes in phosphor-mTOR from cycle training.
Figure 9:
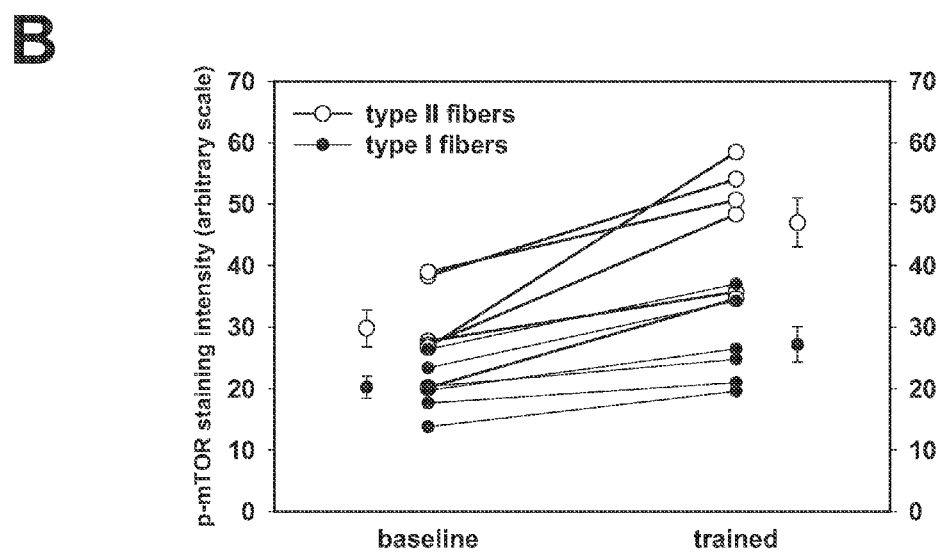

Fiber-specific changes in phospho-mTOR associated with six weeks of stationary cycle training: Activation of mTOR by phosphorylation is associated with protein synthesis regulation (5), and resistance exercise training is usually manifested histologically by increased size of type II fibers (7). We evaluated the change in expression of phospho-mTOR in type I and type II muscle fibers between the baseline and post-training muscle biopsies from our six subjects. FIG. 9 shows the results of these immunohistochemical studies. In the baseline biopsies, the specific phospho-mTOR intensity was 50% higher in the type IT fibers. The exercise training was associated with increased phospho-mTOR in both type I and type II fibers, 34% more in type I fibers and 62% more in type II fibers. In four subjects, both fiber types increased in cross-sectional area, but in the other two both fiber types decreased, and as a group, fiber size was not statistically different after training (type I baseline 6180±900~µm², type 11 baseline 5940±1050, type I trained 6480±823, type IT trained 5820±1040).

Discussion

In the studies reported here, persons at high risk for diabetes because of sedentary life style and a family history of diabetes, were recruited to undergo cycle strength-endurance training of the quadriceps muscle using a stationary cycle with increasing intensity over a six week period. Needle biopsies were obtained from the vastus lateralis and muscle glucose transporters were quantified. SEQ ID NO. 12 (GLUT4) and SEQ ID NO. 16 (GLUT12) were increased by the exercise training, but SEQ ID NO. 10 (GLUT1) did not change, and SEQ ID NO. 24 (GLUT5) decreased at the same time. Mitochondrial markers, phospho-AMPK, and PGC I-α did not change, but phospho-mTOR increased significantly in muscle homogenates. Immunohistochemical studies showed that the increase in SEQ ID NO. 12 (GLUT4) expression occurred in type II fibers (fast twitch, white fibers), bringing the amount of SEQ ID NO. 12 (GLUT4) in those fibers to levels equivalent to the amount found in type I fibers (slow twitch, red fibers) at baseline. Image analysis of digital images of phospho-mTOR expression demonstrated resistance exercise training induced increases in both type I and type ti fibers, but the changes were greatest in type II fibers.

Regular exercise is beneficial to the management of type 2 diabetes (17). Whether the exercise consists predominantly of endurance training or strength training, glycemic control improves (10; 16), as does insulin resistance (29; 54). While, over a short-term neither type of exercise converts one muscle fiber type to another and no new fibers are formed, both can be associated with an increase in the size of the corresponding fibers (3; 24; 35). However, longterm aerobic exercise is associated with a decrease in cross sectional area (1; 30), In addition, both types of exercise are associated with an increase in SEQ ID NO. 12 (GLUT4), the insulin-responsive glucose transporter (14; 24; 31), and an increase in glycogen synthase (24) and muscle glycogen content (9; 14), Endurance training causes an increase in mitochondrial biogenesis and a coincident increase in oxidative enzymes and fatty acid oxidation. These effects are predominantly in red fibers (25; 31). In contrast, strength training does not typically increase mitochondrial production or oxidative enzymes (11; 24; 42). Hosten and coworkers showed that strength training can increase insulin receptors (24), but two key components of the insulin intracellular pathway, IRS-1 and PI3-K, were not increased (24). Endurance training can cause an increase in the ratio of capillaries to red fibers (3; 31). Changes in capillaries are less clear in strength trained individuals (24), even though muscle blood flow is increased after both types of exercise programs (13; 24). Results of studies of exercise training-related changes in intramyocyte triglyceride accumulation have been inconsistent and contradictory (31). There is some evidence that certain types of high-volume resistance training can use intra-cellular triglyceride stores to supply part of the energy.

Reports of exercise training of subjects with type 2 diabetes have consistently shown effects that are qualitatively similar to the adaptations found in non-diabetic subjects. These data suggest that the enhanced insulin action seen after exercise training (either endurance or strength training) is due to increased SEQ ID NO. 12 (GLUT4) expression and may be related to the consequent increased glycogen content of the contracting fiber. The role of mitochondrial biogenesis and fatty acid oxidation may be supplemental in endurance training but do not play a significant role in strength training.

The molecular mediators of muscle adaptation appear to be quite different between endurance training and strength training (5). Endurance training causes an increase in the amount and activity of AMP-activated protein kinase (AMPK) which in turn activates a cascade of intramuscular pathways that increase energy generation (18). Peroxisome proliferatoractivated receptor-gamma co-activator 1 alpha (pGC-1α) is a key subsequent step in the stimulation of mitochondrial biogenesis (4). In contrast, resistance training does not cause an increase in mitochondrial biogenesis, but stimulates increased protein synthesis in muscle fibers, resulting in increased size of the fibers (7). Substantial evidence suggests that resistance exercise-induced adaptive muscle growth is dependent on the activation of a serine-threonine protein kinase, mammalian target of rapamycin (mTOR) and its downstream targets (7). The AMPK pathway and the mTOR signaling pathways may interact such that the AMPK/PGC-1α cascade suppresses the high energy consuming mTOR protein synthetic pathway (32). Combining endurance training with resistance training may suppress the muscle growth and strength enhancement seen with resistance training alone, but it does not appear that resistance training inhibits endurance training-related mitochondrial biogenesis (32). Baar has suggested that even though the mTOR pathway may also reciprocally block the AMPK pathway, the clinical observations do not support strength training suppressing endurance adaptation (5).

Paradoxically, activation of the raptor/mTOR/S610 pathway has recently been shown to induce insulin resistance in one system (45; 46). Shah and Hunter have shown in cells from patients with tuberous sclerosis, activation of the mTOR pathway can induce insulin resistance by serine phosphorylation and downregnlation of IRS-1/IRS-2 (46). This observation in this limited cell culture system is not consistent with the in vivo demonstrations that strength training ameliorates insulin resistance (10; 16; 29; 54).

There was no evidence of a shift of type II to type I fibers. Periods of three to nine months of training were used by several investigators, but training periods as short as one week have been shown to substantially increase mitochondrial oxidative enzymes in the muscle groups used in training (47; 48). Studies in rats by Takekura and Yoshioka showed that short-term resistance training predominantly increased the size of type II fibers, whereas endurance exercise exerted its effects on fiber size more on type I fibers (52).

SEQ ID NO. 12 (GLUT4) protein in muscle is increased by exercise training (15). Houmard and coworkers found that SEQ ID NO. 12 (GLUT14) content of vastus lateralis muscle biopsies nearly doubled after 14 weeks of training (27) and more recently showed a more than doubling of the SEQ ID NO. 12 (GLUT4) content of vastus lateralis homogenate after only 7 days of intense cycle ergometer training (26). Daugaard and coworkers evaluated individual fiber type expression of SEQ ID NO. 12 (GLUT4) and found that two weeks of primarily endurance training resulted in increased SEQ ID NO. 12 (GLUT4) in type I fibers only (12). The increased SEQ ID NO. 12 (GLUT4) induced by training is rapidly lost with detraining. McCoy and coworkers prevented six distance runners from exercising for 10 days and measured a one third drop in SEQ ID NO. 12 (GLUT4) in vastus lateralis homogenate (38).

In the training and/or detraining studies reviewed where both SEQ ID NO. 12 (GLUT4) and mitochondrial enzymes were measured, there was a tight correlation of both either increasing or decreasing together (6; 12; 38). Laurie Goodyear and coworkers trained rats for six weeks and showed that muscle SEQ ID NO. 12 (GLUT4) protein was increased 30% but noted that virtually all of the increase was at the plasma membrane in the basal state (21). SEQ ID NO. 10 (GLUT1) content and subcellular distribution was not altered by training. Banks and coworkers demonstrated increased muscle SEQ ID NO. 12 (GLUT4) in exercise trained obese Zucker rats (6). Insulin-stimulated uptake of 3-O-methyl-D-glucose was improved and closely correlated with increased mitochondrial enzyme activity (citrate synthase) and SEQ ID NO. 12 (GLUT4) protein content.

Exercise training studies of mice and rats have shown that a cascade of mitochondrial biogenesis events in both nuclear and mitochondrial genes are activated via peroxisome proliferator-activated receptor-gamma co-activator 1 alpha (pGC-1a) (44; 51). Activation of peroxisome proliferator-activated receptor-delta (PPARδ) may be a key step in this process (56). Low levels of PGC-1α in muscle are associated with insulin resistance in humans and are induced by feeding a high fat diet in mice (34). Exercise training in mice increases muscle PGC-1α and prevents the full effect of the high fat diet on obesity and insulin resistance (34). Overexpression of PGC-1a in cultured myocytes by transfection with adenovirus resulted in a switch to complete fatty acid oxidation (34). Wu, et ai, recently generated transgenic mice that selectively expressed in skeletal muscle a constitutively active form of calcium/calmodulin-dependent protein kinase IV (CaMKIV) (57). Muscle from these mice showed increased mitochondrial DNA, increased mitochondrial number, increased mitochondrial enzymes involved in electron transport and fatty acid oxidation and increased stamina. In these mice CaMK1V induced expression of PGC-1α, and in their cultured myocytes activated the PGC-1α promoter (57).

Microarray studies suggest muscle adaptation to some types of exercise is tied to mitochondria-related gene expression. A bout of exhaustive exercise in man causes a significant increase in mRNA acutely in over 100 genes as evaluated n microarrays (37). The genes stimulated included a number of mitochondrial enzymes, PPARγ, PPARδ, metalothioneins, and nuclear factor subfamily 4A family members (37).

These studies summarized here give strong evidence that endurance exercise training has a direct effect on intramuscular PGC-1a through AMPK. PGC-1α activates cassettes of genes, both nuclear and mitochondrial, resulting in increased mitochondrial biogenesis. At least some of the effects of PGC-1α are mediated through PPARδ and these may include increased SEQ ID NO. 12 (GLUT4) expression and suppression of SEQ ID NO. 24 (GLUT5) expression. Any impact of exercise on muscle fiber capillaries is likely mediated through other nuclear factors such as hypoxia-inducible-factor-1 (HIF-1) (55).

Activation of AMPK occurs transiently with each exercise bout and, in humans, baseline phospho-AMPK is increased chronically in response to exercise training. Muscle contraction acutely in results phosphorylation of the α subunit of 5'-AMP-activated protein kinase (AMPK) presumedly primarily via. AMPK-kinase (AMPKK) (23). Exercise training in rats has been shown to cause an increase in AMPKK protein, but the activity of AMPKK is diminished as measured by phosphorylation of AMPK. In rat treadmill training studies from Winder's group, neither AMPK or basal phospho-AMPK are increased by the endurance exercise (23; 28; 53). They found that both basal and electrically stimulated muscle contraction acute activation (phosphorylation) of AMPK was similar in trained and sedentary rats (28). However, the reports of endurance training in humans demonstrated some key differences. Nielsen and coworkers in Copenhagen evaluated basal and exercise-stimulated phospho-AMPK by western blots in vastus lateralis muscle from seven endurance-trained athletes and seven sedentary subjects (41). Biopsies were performed after an overnight fast, before and after a 20 minute bout of exercise on a cycle ergometer at 80% $VO_2$max. In the trained subjects, phosphorylation of AMPK was nearly twice that of the sedentary subjects and the activity of AMPK was 34% higher than the sedentary subjects, even though neither of these differences reached statistical significance. Frosig and coworkers also of Copenhagen performed a classic study where they had eight healthy young men train only one leg for three weeks (18). The contralateral leg became the control leg. They found that the trained muscle had increased 0.1 subunit by 41% and the basal phospho-AMPK was 74% higher in the trained muscle than the control muscle. These biopsies were performed at least 15 hours after the last training session.

The human studies form Nielsen, et at, demonstrated acute stimulation of phosphorylation of AMPK and stimulation of the 0.1 kinase activity of AMPK by 20 minutes at 80% of $VO_2$max. Their data showed that the trained athletes had higher baseline AMPK phosphorylation and activity, but that the augmentation by exercise was less than in the nontrained subjects (41). The results from Frosig's studies of one leg training showed quantitatively larger changes that were consistently statistically significant (18). The 0.1 subunit protein was 25% higher, basal phospho-AMPK was 74% higher, and basal AMPK activity associated with the 0.1 subunit was twice that of the contralateral control muscle. Frosig and coworkers felt that the increased basal AMPK phosphorylation and activity were training effects rather than a residual effect of the last exercise bout (18). They repeated their observations at 55 hours postexercise and found that the increased basal AMPK activity persisted, suggested that the AMPK activity "is probably chronically elevated in skeletal muscle during periods of regularly repeated endurance exercise".

Regular exercise benefits patients with type 2 diabetes and is an effective measure to prevent or delay the onset of diabetes (33). Either aerobic exercise or strength training are beneficial in that they both improve insulin resistance and are associated with significant improvement in glycemia in diabetic patients. Aerobic or endurance training exerts most of its effects on muscle through increased mitochondria and oxidative capacity predominantly in type I (red, slow twitch) fibers, whereas resistance or strength training largely affects type II (white, fast twitch) fibers by increasing net protein synthesis and causing muscle hypertrophy. The only shared effects of these two types of exercise training previously reported are an increase in the muscle content of the insulin- and contraction-responsive glucose transporter, SEQ ID NO. 12 (GLUT4), and a consequent increase in muscle glycogen.

The results of the strength-endurance training of formerly sedentary subjects using a stationary cycle that we report here show increased SEQ ID NO. 12 (GLUT4) and SEQ ID NO. 16 (GLUT12) expression and a coincident decrease in GLUTS. These glucose transporter changes occurred with no change in mitochondria as quantified by cytochrome c and no alteration in either phospho-AMPK or PGC1a, the major regulators of mitochondrial biogenesis. Instead, the muscle hypertrophy-related protein synthetic pathway was stimulated as indicated by a training-induced near doubling of phospho-mTOR. The increase in phospho-mTOR occurred in both type I and type II muscle fibers, but were relatively more in type IT fibers. The SEQ ID NO. 12 (GLUT4) increase was also predominantly in type II fibers. We conclude that our stationary cycle exercise program resulted in increased inulin-responsive glucose transporter expression in trained muscles via resistance exerciseresponsive pathways predominantly in type II muscle fibers and there was no involvement of the mitochondrial biogenesis system in the muscle adaptation to the program. These data suggest that the beneficial effect of strength-endurance training in insulin resistance and diabetes management may be more closely tied to SEQ ID NO. 12 (GLUT4) expression and the consequent increased glycogen storage, and less related to changes in mitochondrial glucose and fatty acid oxidation. In summary: the physiological alterations observed in this study represent a unique finding in that this type of training (strength-endurance) may be more typical of strength training among very sedentary subjects compared to endurance training Figure Captions FIG. 1. Serial dilutions of SEQ ID NO. 10 (GLUT1) and SEQ ID NO. 12 (GLUT4) on immunoblots. Shown here are serial dilution immunoblots of SEQ ID NO. 10 (GLUT1) and SEQ ID NO. 12 (GLUT4). The first lane of each blot contains 10–L of the cell free translation protein production as described in Methods, diluted 1:1,000. The fmoles/lane as indicated was calculated based on the protein content of the specific band determined by the Agilent Bioanalyzer 21 OOe and a deduced molecular weight of 44,244.

FIG. 2. Change in muscle SEQ ID NO. 12 (GLUT4) mRNA by stationary cycle training. Six subjects underwent muscle biopsy before and after six weeks of supervised, increasing intensity training on a stationary bike. RNA was isolated and mRNA was quantified using real-time quantitative peR as described. One sample was degraded and not usable. The data shown here are means of three separate assays for each sample. The 22% increase was significant at $p=0.05$ by paired nest.

FIG. 3. Change in muscle SEQ ID NO. 12 (GLUT4) protein by stationary cycle training. Immunoblots of muscle homogenates and SEQ ID NO. 12 (GLUT4) standards were quantified by image analysis in four separate experiments. The amount of muscle homogenate applied to each lane for SEQ ID NO. 12 (GLUT4) measurements was 10~g membrane protein. Each subject is indicated by his/her subject code (EXOI through EX06). The baseline sample is indicated by "A" and the post-training sample by "B" for each subject. The blot shown is typical and the graph shows the means of four studies for each sample. The 66% increase was significant at the $p<0.01$ level with paired t-test.

FIG. 4. Changes in SEQ ID NO. 24 (GLUT5) and SEQ ID NO. 16 (GLUT12) induced by six weeks of stationary cycle training. Similar to the studies of SEQ ID NO. 12 (GLUT4) expression, SEQ ID NO. 10 (GLUT1), GLUTS, and SEQ ID NO. 16 (GLUT12) were quantified on immunoblots with specific protein standards. The blots shown are typical of several studies. Each subject is indicated by hislher subject code (EXOI through EX06). These blots included 20 flg membrane protein in each lane. The graphs (Panels B, C, and D) represent means of four separate analyses for GLUTS and SEQ ID NO. 16 (GLUT12), and three for SEQ ID NO. 10 (GLUT1). The 104% increase in SEQ ID NO. 16 (GLUT12) expression and 72% decrease in GLUTS were each significant at $p<0.01$ by paired t-test.

Figure 5:
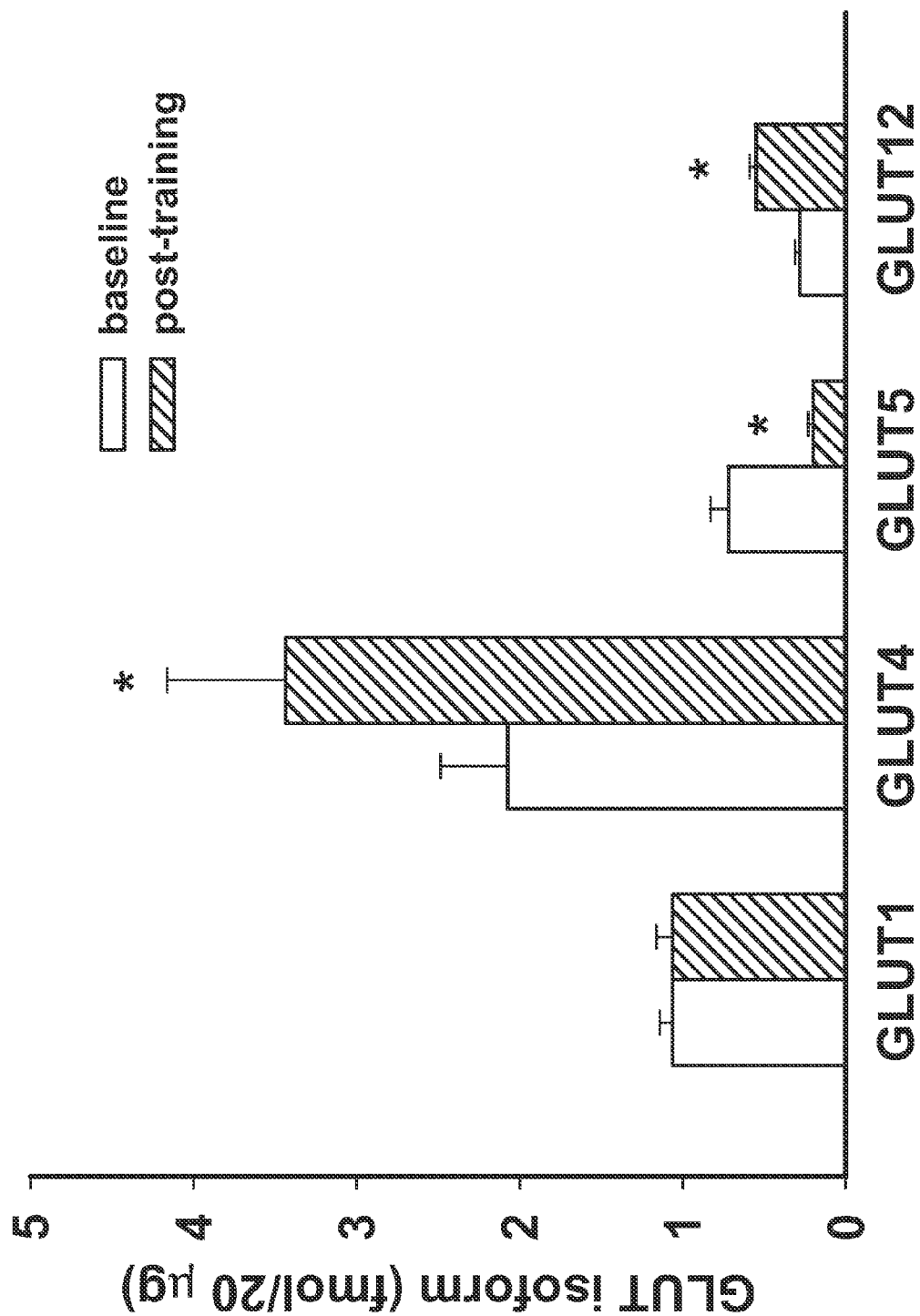
FIG. 5 shows a schematic graphical comparison of changes in muscle glucose transporter expression.

FIG. 5. Comparison of changes in muscle glucose transporter expression: Shown here are the quantification of the glucose transporter protein as fmoles per 20 fig membrane protein applied to the polyacrylamide gel electrophoresis system for immunoblotting. Since each lane for SEQ ID NO. 12 (GLUT4) measurement as shown in FIG. 3 contained 10 flg, the SEQ ID NO. 12 (GLUT4) data in this figure are adjusted to allow direct comparison. Each of these three hexose transporters were significantly different in expression after the training protocol at $p<0.01$ as indicated by the asterisk. The data presented are compiled from at least three separate determinations for each glucose transporter.

FIG. 6. Changes in cytochrome c and PGC-1a by an exercise training program. Immunoblots of cytochrome c and PGC-1u are shown along with a blot showing actin expression as a housekeeper protein. Each subject is indicated by his/her subject code (EXOI through EX06). The baseline sample is indicated by "A" and the post-training sample by "B" for each subject. Cytochrome c expression was not altered by the stationary cycle training program, nor was the mitochondrial biogenesis coactivator, PGC-1a, suggesting that there was little or no aerobic training-related muscle adaptation.

FIG. 7. Changes in phospho-AMPK and phospho-mTOR induced by six weeks of cycle training of sedentary volunteers. Immunoblots of muscle homogenate from vastus lateralis biopsies were probed with antibodies against phospho-AMPK and phospho-mTOR to determine which of these two protein kinase systems were activated by six weeks of progressive training on stationary cycles. Each subject is indicated by his/her subject code (EXOI through EX06). The baseline sample is indicated by "A" and the post-training sample by "B" for each subject. Image analysis showed a non-significant 12% drop in AMPK phosphorylation (panel B) but phosphomTOR increased by 83% (panel. C). The data shown in Panel B are means from three separate experiments and those in Panel C represent the mean of two separate studies for each data point. The increase in phospho-mTOR was significant at $p<0.01$ by paired t-test.

FIG. 8. Muscle fiber-specific changes in SEQ ID NO. 12 (GLUT4) induced by six weeks of cycle training. Panel A displays images from one subject. The top two images are from the pre-training biopsy and the bottom two are from the post-training biopsy. The red image is tagged using antih SEQ ID NO. 12 (GLUT4) as the primary antibody and the blue image from the same section was probed with the anti-human fast myosin monoclonal antibody. The most intense staining in the top SEQ ID NO. 12 (GLUT4) image is in the type I fibers (unstained in the blue image) and the most intense SEQ ID NO. 12 (GLUT4) signal in the post-training image is in the type II fibers (blue positive fibers). The images for each subject were from two corresponding sections prepared and incubated simultaneously on the same slide. The confocal microscope settings were identical for all twelve images shown here. Panel B shows the results of image analysis assessment of the intensity of the fluorescent signal in type I and type IT fibers. Ten fibers of each type in each image were assessed for average intensity using the Quantity One software and the average intensity from those ten fibers was plotted for each data point shown in Panel B. Paired t-tests gave $p<0.01$ for both type I and type IT changes.

FIG. 9. Muscle fiber-specific changes in phospho-mTOR from cycle training. Panel A is similar to Panel A of FIG. 8, except that the primary antibody in the red image was antiphospho-mTOR. Panel B shows the results of quantitative image analysis assessment of the intensity of the fluorescent signal in type I and type II fibers. The image analysis revealed increased signal in both fiber types, but the increase was greater in the type II fibers (+62%) than in the type I fibers (+34%). Paired t-tests gave $p<0.01$ for both type I and type II changes.

Introductory Remarks

Objective. SEQ ID NO. 12 (GLUT4) is the predominant glucose transporter isoform expressed in fat and muscle. In SEQ ID NO. 3 null mice, insulin-stimulated glucose uptake into muscle is diminished but not eliminated, suggesting another insulin-sensitive system was present. Our laboratory previously reported SEQ ID NO. 16 (GLUT12) mRNA represented 6% of the total of muscle-expressed GLUTs (SEQ ID NO. 12 (GLUT4) accounted for 70%) and like SEQ ID NO. 12 (GLUT4), SEQ ID NO. 16 (GLUT12) protein was predominantly expressed in red muscle fibers. These studies were to determine if insulin also caused SEQ ID NO. 16 (GLUT12) translocation in muscle.

Research Design and Methods. Six normal volunteers each underwent euglycemic insulin infusions, muscle biopsies were obtained, fractionated and SEQ ID NO. 16 (GLUT12), SEQ ID NO. 12 (GLUT4), and SEQ ID NO. 10 (GLUT1) content were quantified in the fractions. The impact of phosphatidyl inositol-3 kinase (pI3-K) inhibition on insulin-related translocation of SEQ ID NO. 16 (GLUT12) was determined in cultured myoblasts.

Results. Insulin infusion caused a shift of a portion of SEQ ID NO. 16 (GLUT12) from its intracellular location to the plasma membrane (PM) fraction (17% in PM at baseline, 38% in PM after insulin). Insulin increased SEQ ID NO. 12 (GLUT4) in PM from 13% to 42%. SEQ ID NO. 10 (GLUT)) was 78% in PM at baseline and did not change in response to insulin. L6 myoblasts in culture also expressed and translocated SEQ ID NO. 16 (GLUT12) in response to insulin. Inhibiting PI3-K in L6 cells prevented the movement of SEQ ID NO. 16 (GLUT12) and SEQ ID NO. 12 (GLUT4) to the plasma membrane-enriched fractions.

Conclusions. These data suggest that like insulin's acute effect on SEQ ID NO. 12 (GLUT4) in muscle, insulin causes SEQ ID NO. 16 (GLUT12) to translocate from an intracellular location to the cell surface in normal human skeletal muscle. Translocation of SEQ ID NO. 16 (GLUT12) in cultured myoblasts was dependent of activation of PD-K. We suggest SEQ ID NO. 16 (GLUT12) evolutionarily preceded SEQ ID NO. 12 (GLUT4) and now provides redundancy to the dominant SEQ ID NO. 12 (GLUT4) system in muscle.

Introduction

Increments in insulin concentration and muscle contraction cause the insulin-responsive glucose transporter, SEQ ID NO. 12 (GLUT4), to move from sequestered intracellular locations to the muscle cell surface and to t-tubules where these facilitative glucose transporter proteins allow glucose to move from the extracellular fluid to the interior of the muscle cell (1). Insulin accomplishes this translocation of SEQ ID NO. 12 (GLUT4) proteins through interaction with its cell surface receptor, activating the receptor's intrinsic tryrosine kinase, phosphorylation of insulin receptor substrate-I, and subsequent steps in an intracellular pathway that eventually involves the activation of phosphatidyl inositol 3-phosphate kinase (pI3-K) (1; 2). PI 3-K activates the translocation process that involves fusion of vesicles containing SEQ ID NO. 12 (GLUT4) with the muscle cell surface via a complex interaction of SNAP and SNARE proteins in lipid rafts (3).

More than a decade ago, a SEQ ID NO. 3 knockout mouse was developed and its phenotype characterized. To the surprise of many of us, the SEQ ID NO. 3 null mouse did not develop diabetes and glucose uptake into muscle was still insulin-responsive (4; 5). At that time, it was concluded that there was another glucose transporter isoform in muscle that was translocated in response to insulin. We have recently identified seven glucose transporter isoforms that are expressed in human skeletal muscle, but three of these account for 98% of the mRNA quantified using primers; reverse transcriptase, and real-time peR (6). Of these, GLUT5 is expressed at the cell surface and is predominantly present in type II (white) fibers. SEQ ID NO. 12 (GLUT4) and SEQ ID NO. 16 (GLUT12) are expressed more in type I (red) muscle fibers, and both have amino termini that contain a dileucine motif that is consistent with a predominantly intracellular expression site (7). SEQ ID NO. 15 (GLUT8) also has the dileucine motif in the amino terminus, but its mRNA was quantified at a much lower level than SEQ ID NO. 16 (GLUT12) (6), suggesting that SEQ ID NO. 16 (GLUT12) was a more likely backup isoform to the SEQ ID NO. 12 (GLUT4) translocation system.

To test the hypothesis that SEQ ID NO. 16 (GLUT12) worked in concert with SEQ ID NO. 12 (GLUT4) in augmenting glucose uptake into muse Fe in response to insulin, we performed euglycemic insulin clamp studies in six normal volunteers. Needle biopsies of vastus lateralis muscle were performed in the baseline period and at the end of three hours of insulin infusion that achieved physiological concentrations of insulin in blood. Muscle samples were fractionated by differential centrifugation into low density microsomes and plasma membrane-enriched fractions in which quantitative immunoblots demonstrated that the amount of both SEQ ID NO. 12 (GLUT4) and SEQ ID NO. 16 (GLUT12) in the plasma membrane-enriched fractions more than doubled in response to the insulin infusion.

Quantitative immunoblots suggested that as much as 12% of the insulin-translocatable glucose transporters were accounted for by SEQ ID NO. 16 (GLUT12). To determine if the key intracellular step of activation of PI3-K was also involved in SEQ ID NO. 16 (GLUT12) translocation, we first documented that insulin caused movement to the cell surface in L6 myoblasts in culture and demonstrated that LY294002, a PI3-K inhibitor, prevented SEQ ID NO. 16 (GLUT12) translocation in these cells.

Materials and Methods

Materials: SEQ ID NO. 12 (GLUT4) antibodies (ABI049, goat anti-human) were purchased from Chemicon (Temecula, Calif.). Rabbit anti-h SEQ ID NO. 16 (GLUT12) antibodies (RDI-SEQ ID NO. 10 (GLUT1)$_2$abrx) were purchased from Research Diagnostics (Flanders, 3). Alpha Diagnostic International was the source of antih SEQ ID NO. 10 (GLUT1) antibodies (GT12-A). The corresponding immunization peptides (GT41-P, GT122-P GT13-P) were obtained from Alpha Diagnostic International. SuperSignal west pico chemoluminescence substrate was purchased from Pierce (Rockford, Ill.). LY294002 was obtained from Sigma (St. Louis, Mo.). All other chemicals were reagent grade. L6 cells (ratderived myocytes) were obtained from American Type Culture Collection (Manas3 as, VA).

Subject selection: Six volunteers were recruited that were of normal weight and had no family history of diabetes. Subject characteristics are shown in Table 1. The protocol and the consent document were approved by the Institutional Review Board of East Tennessee State University.

Euglycemic insulin clamp studies: Insulin infusion studies were performed essentially as previously described (8; 9) except no isotope or somatostatin were used in this study. Mter an overnight fast, subjects were maintained in quiet recumbency for two hours to minimize the effects of muscular activity on protein subcellular localization. After a baseline muscle biopsy, a constant insulin infusion was performed at 40 mU/m2/min for three hours. A second muscle biopsy was performed on the contralateral side in the last 10 minutes of the insulin infusion period.

Muscle biopsies: Percutaneous needle biopsies of vastus lateralis were performed using a 5 mm Bergstrom-Stille needle under suction after an overnight fast and two hours of quiet recumbency as previously described (6). A 50-100 mg specimen was quickly blotted and the entire sample was frozen in liquid nitrogen for later analysis.

Fractionation of muscle microsamples: We have made minor modifications of our previously described techniques (10). Briefly, 50 mg muscle is removed from the −80° C. freezer and slowly thawed on ice. The muscle is homogenized in 1.0 ml Buffer A (250 mM sucrose, 20 mM HEPES, pH 7.4) with 5 µL protease cocktail (Cocktail Kit Pierce #78410) added. Initial homogenization is 30 seconds with a Pellet Pestle Motor (Kontes). The homogenate is passed through a BD Falcon 100 µm Cell Strainer and after adding 100 µL Buffer B (3M KCl, 250 roM sodium pyrophosphate), is spun at 227,000×g for 30 minutes. The pellet is resuspended in 1.0 mL of Buffer A with protease cocktail using the Pellet Pestle Motor again for 30 seconds. This sample is then spun at 12,000×g for 20 minutes. The pellet is resuspended in 200 µl, Boston Bioproducts Triton Lysis Buffer with Protease Inhibitor (BP-117) using the Pellet Pestle Motor. This sample is designated PM, the plasma membrane-enriched fraction. The supernate is removed and spun at 227,000×g for 30 minutes. The resulting pellet is also resuspended in 200 µL Boston. Bioproducts Triton Lysis Buffer, and is designated LDM, the low density microsomes fraction. PM protein content averaged 139±7 µg and LDM contained 265±8 µg protein. In studies performed on human control muscle sample fractions, the PM fraction contained 80% of the immunological signal for the plasma membrane marker Na/K+ ATPase α-I (05-369 from Millipore). LDM contained 67% of the golgi marker mannosidase II (AB3712 from Chemicon).

Fractionation of L6 muscle cells: L6 cells were obtained from ATCC and cultured in D.MEM medium with 10% fetal bovine serum with subculturing every three to five days. For the studies described below, cells were grown to near confluence in 100 mm dishes. Cells were harvested in 1 mL homogenization Buffer A containing 5 µL protease inhibitors using a rubber policeman. The remainder of the technique is the same as muscle microsamples. The yield of protein averaged 199±14 µg for PM and 419±22 µg for LDM.

Immunoblot technique: Immunoblotting was performed essentially as previously described (11). In general, 10-20 µg protein from muscle homogenate or fractions was separated on a 10% polyacrylamide gel using the Laemmli system (12), transferred to a nitrocellulose membrane, subjected to blocking with 2.5% non-fat dry milk in phosphate-buffered saline, incubated with a validated dilution of one of the anti-GLUT antibodies above including 1.25% milk, and developed with the enhanced chemiluminescence reagent and X-ray film. Image analysis was performed on scanned film digital files using Quantity One version 4.5.2 software from Bio-Rad (Hercules, Calif.). The specificity of the antibodies employed for GLUT1 SEQ ID NO. 12 (GLUT4), and SEQ ID NO. 16 (GLUT12) was empirically tested using blots that included control muscle homogenates and specific chimeric protein standards. Each antibody was tested with these blots in the absence and presence of the immunization peptide for SEQ ID NO. 10 (GLUT1), SEQ ID NO. 12 (GLUT4), and SEQ ID NO. 16 (GLUT12), separately. For these specificity studies, each gel lane contained 20-40 µg homogenate, the antibodies were at 1: 500 final dilution (2 µg/mL), and the immunization peptide at 10 µg/mL. Prior to incubation with the blot, the antibodies and each peptide were incubated at 20° C. for 20 minutes. In each case, the antibody specifically labeled a band in muscle homogenate with mobility of apparent molecular weight of 55 kDa, 45 kDa, and 58 kDa for SEQ. ID NO. 10 (GLUT1), SEQ ID NO. 12 (GLUT4), and SEQ ID NO. 16 (GLUT12), respectively. The apparent molecular weight for all of the specific chimeric protein standards was 41 kDa. The immunizing peptides only inhibited labeling with their specific antibody in muscle homogenate and the chimeric protein standards.

Glucose transporter protein standards: The construct SEQ ID NO. 1 was generated to express a soluble chimeric protein comprised of ovalbumin. and a SEQ ID NO. 10 (GLUT1) epitope tag. Chicken ovalbumin (nt 66-68, 81-1223; Genbank accession V00383) was amplified from pOV2 (generously provided by Dr. Michel Sanders of the University of Minnesota) using the primers SEQ ID NO. 19 and SEQ ID NO. 20 (Table 2) and TA-cloned into pCR T7 TOPO (Invitrogen, Carlsbad, Calif.). As the ovalbumin coding region in pOV2 is incomplete, missing the first five codons and first by of the sixth codon, the sense primer SEQ ID NO. 19 was designed to restore the initiator ATG and complete the sixth codon, while excluding the second through fifth codons. The antisense primer was complimentary to ovalbumin nt 1201-1222 and included sequence encoding the Cterminal 12 amino acids of human SEQ ID NO. 10 (GLUT1)(aa 481-492; SwissProt accession P11166). Codons were optimized for use of *E. coli* for translation. Chimeric protein was expressed using a coupled in vitro transcription/translation system (Active Pro In Vitro Translation kit, Ambion, Inc.) according to the manufacturer's protocol. The amount of chimeric protein generated was then quantified using electrophoresis with the Agilent Bioanalyzer 2100e. The ova-GLUT1 fusion protein had a deduced molecular weight of 44,244 daltons and migrated as a discrete band, which represented 3.5% of the total protein present. Further purification was not done when the product was used as a standard in gel electrophoresis and immunoblotting.

The other chimeric constructs used in this study (ova-GLUT4 and ova-GLUT12) were generated using the same protocol as for ova-GLUT1, with the exception that the antisense primer was changed to correspond to the appropriate carboxy-terminal sequence (Table 2).

Statistics: All data are presented as mean±standard error of the mean. Significant differences were inferred when p<0.05 using t-test or paired t-test. Statistical procedures were performed using SigmaStat version 3.11 from Systat Software (San Jose, Calif.).

Results

Euglycemic insulin clamp: Six healthy young adults (three male, three female) achieved a physiological increment in plasma insulin concentration (Table 3). From a baseline insulin concentration of 28±7 pmol/L, the infusion of insulin at 40 mU/m2/min caused an increase to 343±21 pmol/L. To maintain a blood glucose concentration of 85 mg/dL in the steady state period of the insulin infusion, a mean glucose infusion rate of 8.87 mg/kg·min was necessary.

Insulin-induced increase in SEQ ID NO. 12 (GLUT4) in the plasma membrane-enriched muscle fraction: In the baseline muscle biopsies, SEQ ID NO. 12 (GLUT4) protein was distributed 13% in the plasma membrane enriched fractions. At the end of the insulin infusion, the SEQ ID NO. 12 (GLUT4) distribution had changed dramatically to 42% in the plasma membrane-enriched fractions. FIG. 1 shows a composite of several representative immunoblots of the two fractions, low density microsomes (LDM) and plasma membrane-enriched (PM), from the baseline and the insulin infusion muscle samples for each subj eel. Immunoblots typically included 10 µg of protein in each lane. The calculation for percent of SEQ ID NO. 12 (GLUT4) content in the PM fraction used the image analysis generated fmol/lane multiplied by the total protein content of the fraction. The mean yield from fractionation of 25 mg muscle tissue was 265 µg protein in LDM and 139 µg in PM. FIG. 2 displays the mean data from image analysis of immunoblots from three separate determinations for each individual's baseline and insulin infusion plasma membrane-enriched fraction content of SEQ ID NO. 12 (GLUT4) in the left panel. In each subject, the SEQ ID NO. 12 (GLUT4) content of the PM fraction at least doubled.

Insulin-induced increase in SEQ ID NO. 16 (GLUT12) in the plasma membrane-enriched muscle fraction: FIG. 1 also displays SEQ ID NO. 16 (GLUT12) immunoblots for each individual subject. Image analysis quantification of SEQ ID NO. 16 (GLUT12) in the PM fraction in the baseline samples averaged 17%. After insulin infusion, SEQ ID NO. 16 (GLUT12) protein was shifted to 38% in the plasma membrane-enriched fractions. The distribution of SEQ ID NO. 12 (GLUT4) and SEQ ID NO. 16 (GLUT12) in the baseline and post-insulin infusion were very similar. FIG. 2 (right panel) displays the mean data for three separate studies of SEQ ID NO. 16 (GLUT12) expression in the fractionated samples. The SEQ ID NC). 16 (GLUT12) content of the PM fraction more than doubled in four of the six subjects, with the minimum response being an increase of 60%.

The impact of insulin infusion of the distribution of GLUT1 in muscle fractions: The same fractions that were used for SEQ ID NO. 12 (GLUT4) and GLUT12 immunoblots were subjected to SDSpolyacrylamide electrophoresis, transfer to membranes, and incubation with anti-h GLUT1 antibodies to determine if insulin infusion caused evidence of a shift of the SEQ ID NO. 10 (GLUT1) content from one pool to another. FIG. 3 shows an image of a typical immunoblot for SEQ ID NO. 10 (GLUT 1). In contrast to the results with SEQ ID NO. 12 (GLUT4) and SEQ ID NO. 16 (GLUT12), there was no change in the intensity of the SEQ ID NO. 10 (GLUT1) signal in either the LDM or PM fractions after the insulin infusion. Adjusting for the protein content of the fractions, the baseline PM fractions contained 78±7% of the SEQ ID NO. 10 (GLUT 1) and the post-insulin infusion PM fractions contained 79±9%. These data are the mean±standard error for subjects 1-5. Subject 6 had inadequate samples remaining to quantify the SEQ ID NO. 10 (GLUT1) content after the insulin infusion.

Comparison of muscle expression of SEQ ID NO. 12 (GLUT4) and SEQ ID NO. 16 (GLUT12) proteins: FIG. 4 displays representative immunoblots of muscle homogenates from gel electrophoresis that included known standards for SEQ ID NO. 12 (GLUT4) (top blot) and SEQ ID NO. 16 (GLUT12) (lower blot). From image analysis of digitized films of at least three separate experiments using muscle homogenates from the same six normal volunteers, the absolute amount of each of these two isoforms were quantified and compared. Muscle homogenates yielded approximately 600 µg protein from 25 mg muscle. These six normal subjects muscle biopsies were quantified to contain SEQ ID NO. 12 (GLUT4) at 3.74±0.33 fmoles/mg muscle and SEQ ID NO. 16 (GLUT12) was expressed at 0.51±0.12 fmoles/mg muscle. These data suggest that SEQ ID NO. 16 (GLUT12) represents about 12% of the potentially translocatable glucose transporters in normal skeletal muscle. The ratio of SEQ ID NO. 12 (GLUT4) to SEQ ID NO. 16 (GLUT12) protein (3:1) was less than the ratio of mRNA's (0.12:1) previously reported (6). The data from muscle fractions gave similar ratios of SEQ ID NO. 12 (GLUT4) and SEQ ID NO. 16 (GLUT12) protein. Adding the amount of SEQ ID NO. 12 (GLUT4) or SEQ ID NO. 16 (GLUT12) in LDM and PM together also gave a ratio of expression of 8:1.

Insulin-stimulated translocation of SEQ ID NO. 12 (GLUT4) and SEQ ID NO. 16 GLUT12) in L6 myoblasts is prevented by the phosphatidyl inositol-3 kinase inhibitor, LY294002. In order to determine if the mechanism of SEQ ID NO. 16 (GLUT12) movement to the cell surface of muscle was similar to the mechanism of SEQ ID NO. 12 (GLUT4) translocation, we evaluated insulin-stimulated translocation of these proteins in a rat skeletal muscle-derived cell line previously demonstrated to respond to insulin (13). L6 cells have been used extensively to investigate translocation of SEQ ID NC). 12 (GLUT4) and have been demonstrated to have PI3-K activation as an essential step in the insulin intracellular pathway leading to stimulation of glucose uptake (14; 15). After having undergone serum starvation for 4 hours, L6 cells were pretreated with PI3-K inhibitor LY294002 at concentration of 0, 1 uM, 10 uM and 100 uM for 20 minutes and then incubated in the presence or absence of 10 ng/mL insulin for additional 20 minutes. Cells were then harvested using a rubber scraper in Buffer A and homogenized using a hand-held Kontes homogenizer. After centrifugation (as described in Methods) to separate each sample into low density microsomes (LDM) and plasma membrane-enriched (PM) fractions, 10 or 20 µg protein aliquots were subjected to polyacrylamide electrophoresis and immunoblotting. Panel A of FIG. 5 displays representative immunoblots of the fractions. These immunoblots demonstrate that insulin caused translocation of both SEQ ID NO. 12 (GLUT4) and SEQ ID NO. 16 (GLUT12) to the plasma membrane-enriched fractions and that the PI3-K inhibitor prevented this from happening. Panels B and C show summary data of dose-response studies for both SEQ ID NO. 12 (GLUT4) and Glut12 translocation inhibition by LY294002. The bars represent the mean and standard error data from three to five separate experiments. We found that LY294002 at lower concentrations actually stimulated translocation in the absence of insulin perhaps acting as a partial agonist at 1µ. However, at each concentration used (including 1~), there was inhibition of insulin-induced translocation.

Discussion

SEQ ID NO. 12 (GLUT4) is the predominantly expressed glucose transporter in normal muscle. Based on mRNA data, SEQ ID NO. 13 (GLUT5) and SEQ ID NO. 16 (GLUT12) are expressed in muscle at higher levels than GLUT1, SEQ ID NO. 11 (GLUT5), SEQ ID NO. 15 (GLUT5), and GLUT1 (6). Like SEQ ID NO. 12 (GLUT4), SEQ ID NO. 16 (GLUT12) is expressed at higher levels in type I muscle fibers (6) and is predominantly intracellular in its subcellular localization. We show here that in normal human muscle, both SEQ ID NO. 12 (GLUT4) and SEQ ID NO. 16 (GLUT12) move from a largely-intracellular location to the plasma membrane fraction in response to a euglycemic increase in blood insulin concentration. In contrast, SEQ ID NO. 10 (GLUT1) is predominantly in the plasma membrane fraction at baseline and does not change its distribution in response to insulin infusion. In vitro experiments using L6 myoblasts in culture demonstrated that insulin also caused a shift of SEQ ID NO. 12 (GLUT4) and SEQ ID NO. 16 (GLUT12) from an intracellular location to the plasma membrane fraction. This translocation was blocked by inhibiting phosphatidyl inositol 3-kinase (PI3-K), suggesting, at least in this system, that the translocation of SEQ ID NO. 16 (GLUT12) also requires PI3-K stimulation. These studies did not attempt to resolve the question whether SEQ ID NO. 12 (GLUT4) and SEQ ID NO. 16 (GLUT12) are in the same vesicle or separate vesicles that are translocated by similar pathways of insulin action.

Since 2000, there have been seven members added to the family of mammalian facilitative glucose transporters and a consensus conference was convened in 2001 to standardize the terminology (16). These fourteen proteins have been subdivided into three separate classes based on structure and function. While there are big gaps in the knowledge about the novel GLUTs, several are expressed in human muscle. These are SEQ ID NO. 15 (GLUT5) GLUT11, and SEQ ID NO. 16 (GLUT12). GLUT5 is a fructose transporter and is a member of the Class 11 of glucose transporters that also includes GLUT7, GLUT9, and GLUT11. Of the novel GLUTs, only SEQ ID NO. 14 (GLUT6), SEQ ID NO. 15 (GLUT8), and GLUT11 have had the specificity of glucose transport evaluated. Two of these (SEQ ID NO. 14 (GLUT6) and GLUT11) transport both fructose and glucose (7). Tissue expression has been determined in all but GLUT7, but subcellular localization of the novel GLUTs has been largely by deduction from the amino acid sequences containing dileucine motifs at the amino- or carboxy-terminus. GLUT10 and GLUT11 have no dileucine motif, whereas it was deduced that SEQ ID NO. 14 (GLUT6), GLUT7, SEQ ID NO. 15 (GLUT8), GLUT9, and SEQ ID NO. 16 (GLUT12) are predominantly intracellular in the basal state (7). Regulation by insulin was not known, other than for SEQ ID NO. 16 (GLUT12) where it appears that insulin does not cause translocation in MCF-7 cells in culture (17). The number of facilitative glucose transporters is not likely to increase any further since the search for homologous genes has already been done on a fairly complete human genome database (7). The transport specificity, tissue and subcellular localization, and the acute and chronic regulation of these novel transporter identified in the past ten years will be important new information over the next few years.

Rogers and coworkers first identified SEQ ID NO. 16 (GLUT12) in MCF-7 human breast cancer cells by its homology with SEQ ID NO. 12 (GLUT4) (17). SEQ ID NO. 16 (GLUT12) has 29% amino acid identity with SEQ ID NO. 12 (GLUT4). They demonstrated SEQ ID NO. 16 (GLUT12) in skeletal muscle, adipose tissue, small intestine, and placenta by immunoblotting (17; 18). On the basis of perinuclear localization in MCF-7 cells and the presence of di-leucine motifs near the amino and carboxy termini, Rogers speculated that SEQ ID NO. 16 (GLUT12) might be part of a second insulin-responsive glucose transport system (17). Rogers' group has shown SEQ ID NO. 16 (GLUT12) expression in prostate cancer and breast cancer, whereas it is absent in normal prostate and is expressed at very low levels in normal breast tissue (19; 20). Even though SEQ ID NO. 16 (GLUT12) was early identified as a potential candidate for a second insulin-responsive glucose transporter in muscle and fat, there have not yet been any reports of insulin-induced translocation of SEQ ID NO. 16 (GLUT12) in either cultured cells or in vivo.

Macheda and others of Rogers' group showed an interesting pattern of muscle glucose transporter expression in developing rat embryos (21). They demonstrated SEQ ID NO. 16 (GLUT12) in heart beginning at 15 days gestation and in skeletal muscle from 17 days gestation (21). This SEQ ID NO. 16 (GLUT12) expression preceded the appearance of SEQ ID NO. 12 (GLUT4) in these tissues by six and four days, respectively (22).

We have previously quantified the mRNA expression of members of the GLUT family in normal human muscle (6). In these studies, we found detectable mRNA for SEQ ID NO. 10 (GLUT1), SEQ ID NO. 11 (GLUT3), SEQ ID NO. 15 (GLUT5), and GLUT11, but much higher concentrations of message for SEQ ID NO. 12 (GLUT4), GLUT5, and SEQ ID NO. 16 (GLUT 12). Immunohistochemistry of normal muscle showed strong expression of SEQ ID NO. 12 (GLUT4) and SEQ ID NO. 16 (GLUT12) in type 1 fibers, and GLUT5 was expressed more intensely in type 2 fibers (6). The muscle protein expression data in this report show a ratio of 8:1 for SEQ ID NO. 12 (GLUT4): SEQ ID NO. 16 (GLUT12). The previously reported data for mRNA in normal muscle (6) gave a somewhat higher ratio of 12:1, suggesting disparate post-translational processing or differential degradation may playa role in the observed protein concentrations. Because the patterns of expression in the immunohistochemistry studies were so similar for SEQ ID NO. 12 (GLUT4) and SEQ ID NO. 16 (GLUT12), and both are thought to be predominantly intracellular in the basal state, it was speculated at that time that SEQ ID NO. 12 (GLUT4) and SEQ ID NO. 16 (GLUT12) might even be colocalized to the same vesicles. In fact, in the studies we report here, the basal distribution and the post-insulin infusion muscle fraction distribution of SEQ ID NO. 12 (GLUT4) and SEQ ID NO. 16 (GLUT12) are very similar.

We performed euglycemic insulin infusions in six normal volunteers and, using modifications of Hirshman's muscle microsample fractionation technique (23), demonstrated a shift of SEQ ID NO. 12 (GLUT4) from the intracellular low density microsome fractions to the plasma membrane-enriched fractions (pM). In the baseline: muscle samples, 13% of SEQ ID NO. 12 (GLUT4) was in the PM fractions, whereas at the end of the insulin infusion, an average of 42% was in the PM fractions. These muscle SEQ ID NO. 12 (GLUT4) translocation data are very similar to the human muscle SEQ ID NO. 12 (GLUT4) translocation data reported by Kelley (24), by Garvey (25), and by Zierath (26). Zierath and coworkers and Kelley and coworkers used insulin infusion rates that were the same as those that we used and achieved similar physiological insulin concentrations of 450-600 pmol/L. Zierath demonstrated a 60% increase in SEQ ID NO. 12 (GLUT4) in the muscle plasma membrane fractions after the euglycemic insulin infusion (26). Kelley demonstrated in control subjects an 85% increase in sarcolemma-associated SEQ ID NO. 12 (GLUT4) by conthcal microscopy quantitative immunohistochemistry (24). Garvey and coworkers used a ten-fold higher insulin infusion and was able to show a 2.8-fold increase in SEQ ID NO. 12 (GLUT4) in muscle plasma membrane-enriched fractions from control subjects (25). In the studies we report here, the distributions of SEQ ID NO. 16 (GLUT12) in the baseline muscle samples and in the post-insulin infusion samples were very similar to what we saw with SEQ ID NO. 12 (GLUT4). Prior to insulin infusion, the SEQ ID NO. 16 (GLUT12) was 17% in the M fractions and this was increased by insulin to 38%.

Two independent observations suggest that SEQ ID NO. 16 (GLUT12) may have preceded SEQ ID NO. 12 (GLUT4) in evolution. The human GLUT12 gene structure is much simpler than that of SEQ ID NO. 3. SEQ ID NO. 16 (GLUT12) is a larger protein containing 617 amino acids, but the gene possesses only five exons and four introns (17), whereas SEQ ID NO. 12 (GLUT4) has 509 amino acids and its human gene has ten introns (27). The higher number of introns and exons in the SEQ ID NO. 3 gene is consistent with more complexity and more accumulated variations over millennia. The second observation is the rat embryo ontogeny sited above. In the rat embryo, SEQ ID NO. 16 (GLUT12) message appears in heart at 14 days and the protein at 15 days (21), whereas SEQ ID NO. 12 (GLUT4) mRNA appears at about 17 days and the protein is detectable at 21 days (22). In skeletal muscle both appear a little later, with SEQ ID NO. 16 (GLUT12) protein at 17 days (21) and SEQ ID NO. 12 (GLUT4) protein at 21 days (22).

The data presented here show that SEQ ID NO. 16 (GLUT12) is present in human skeletal muscle and is distributed very similar to SEQ ID NO. 12 (GLUT4) between intracellular and cell surface in the basal state. In response to euglycemic insulin infusions that achieved physiological insulin concentrations in blood, substantial amounts of SEQ ID NO. 16 (GLUT12) moved to the muscle plasma membrane-enriched fractions, in a manner that was quantitatively very similar to the effects on SEQ ID NO. 12 (GLUT4). SEQ ID NO. 16 (GLUT12) represents about 12% of the insulin-translocatable glucose transporters in normal muscle. Our data from L6 muscle cells in culture suggest the translocation of SEQ ID NO. 12 (GLUT4) and SEQ ID NO. 16 (GLUT12) both require activation of PI3-K. We conclude that SEQ ID NO. 16 (GLUT12) translocates to the normal muscle cell plasma membrane in response to insulin. SEQ ID NO. 16 (GLUT12) may provide a backup system for SEQ ID NO. 12 (GLUT4) in skeletal muscle and it likely preceded the evolutionary development of SEQ ID NO. 12 (GLUT4).

Figure Captions

Figure 10:
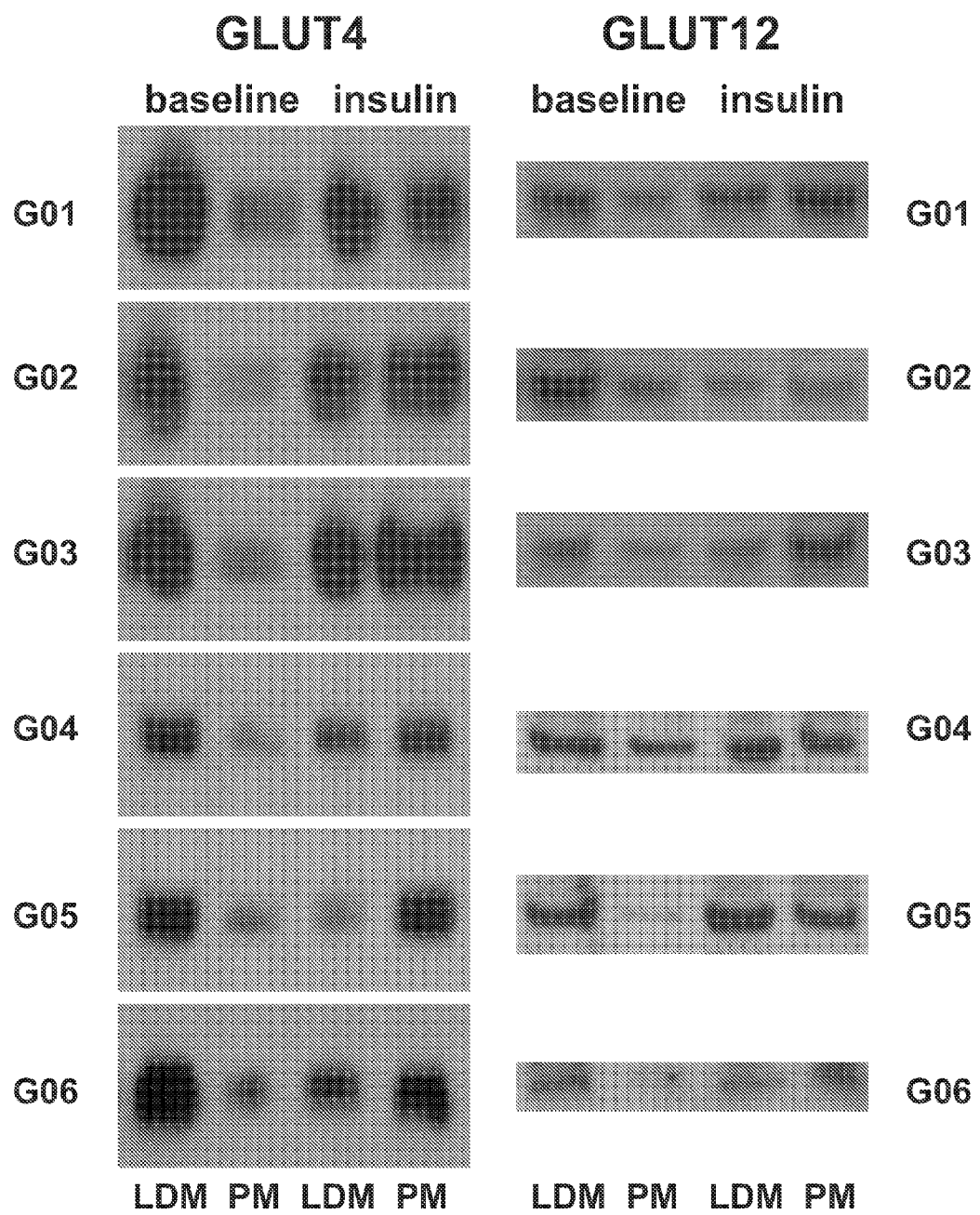
FIG. 10 shows a schematic view of GLUT4 and GLUT12 expression in normal skeletal muscle low density microsomes and plasma membrane fractions before and after insulin infusion.

FIG. 10. SEQ ID NO. 12 (GLUT4) and SEQ ID NO. 16 (GLUT12) expression in normal skeletal muscle low density microsomes and plasma membrane fractions before and after insulin infusion. Percutaneous muscle biopsies were obtained prior to and at the end of three hour euglycemic insulin infusion in six normal volunteers. Muscle homogenates were divided into low density microsomes (LDM) and plasma membrane enriched fractions (PM) by centrifugation as described in Methods. Representative blots are shown for SEQ ID NO. 12 (GLUT4) on the left and SEQ ID NO. 16 (GLUT12) on the right. LDM and PM are designated at the bottom and "baseline" and "insulin" infusion samples are indicated at the top. The blots for SEQ ID NO. 12 (GLUT4) and for SEQ ID NO. 16 (GLUT12) were each performed three times for each subject. The band intensities were quantified and compared to a known SEQ ID NO. 12 (GLUT4) or SEQ ID NO. 16 (GLUT12) standard using image analysis of the digitized films. The total amount of SEQ ID NO. 12 (GLUT4) and SEQ ID NO. 16 (GLUT12) were estimated in each fraction using the quantification per gel lane (10 or 20 μg) and the total protein in the LDM and PM fractions. In the baseline samples, a mean of 13% of the SEQ ID NO. 12 (GLUT4) was in the plasma membrane enriched fractions, and insulin infusion increased the amount in the PM fractions to an average of 42%, Similarly, analysis of the SEQ ID NO. 16 (GLUT12) blots revealed an average of 17% in the PM fraction at baseline and 38% in the PM fraction at the end of the insulin infusion.

Figure 11:
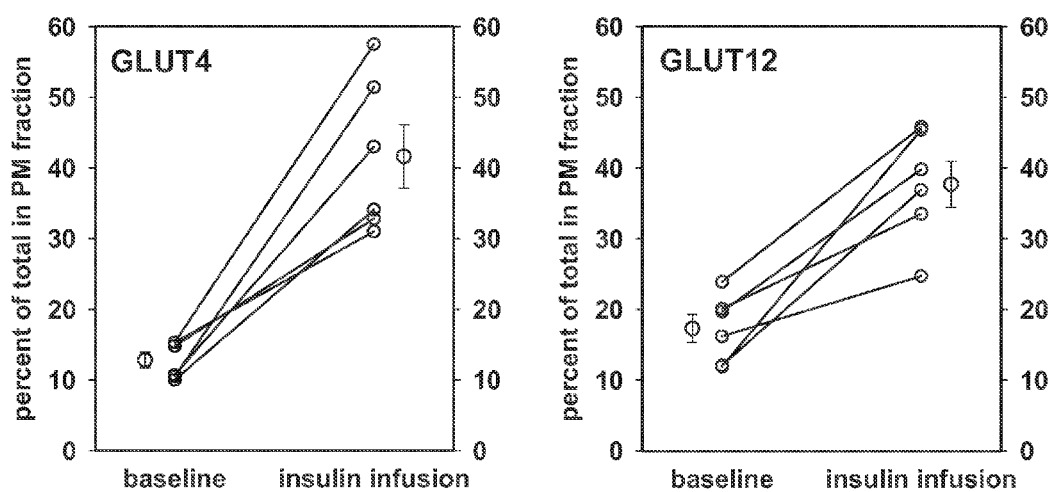
FIG. 11 shows schematical graphical view of the change in GLUT4 and GLUT12 content of a plasma membrane-enriched fraction after insulin infusion.

FIG. 11. Change in SEQ ID NO. 12 (GLUT4) and SEQ ID NO. 16 (GLUT12) content of the plasma membrane-enriched fraction after insulin infusion. Each subject's muscle biopsies were fractionated into low density microsomes (LDM) and plasma membrane-enriched (PM) fractions by differential sedimentation. Immunoblots containing 10 μg per lane were probed with polyclonal rabbit antih SEQ ID NO. 12 (GLUT4) in the presence of a known standard of chimeric ovalbumin SEQ ID NO. 12 (GLUT4) containing the peptide epitope that was used in generating the antibody. Each fraction sample was quantified by image analysis of digitized films in at least three separate studies, The data displayed in this graph represents the means of at least three separate estimates of the SEQ ID NO. 12 (GLUT4) protein content adjusted for the total amount of protein in each fraction. The data displayed in the right panel were generated in the same way as those for SEQ ID NO. 12 (GLUT4) in the left panel, except that the amount of protein per lane was increased to 20 μg, and the antibody used to probe the blots was rabbit antih SEQ ID NO. 16 (GLUT12). The difference between the baseline and the sample at the end of the insulin infusion was significant for both SEQ ID NO. 12 (GLUT4) and SEQ ID NO. 16 (GLUT12) at $p<0.01$ by paired t-test.

Figure 12:
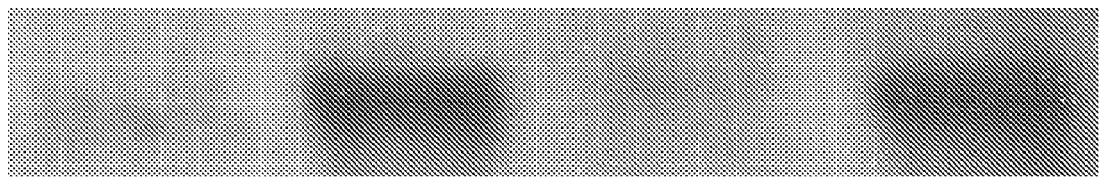
FIG. 12 shows a schematic view of GLUT1 content of muscle fractions after insulin infusion.

FIG. 12. SEQ ID NO. 10 (GLUT1) content of muscle fractions after insulin infusion. As shown in FIG. 1 for SEQ ID NO. 12 (GLUT4) and SEQ ID NO. 16 (GLUT12), low density microsomes (LDM) and plasma membrane-enriched (PM) fractions that were obtained by differential sedimentation were subjected to polyacrylamide electrophoresis and immunoblotting for GLUT1. The image displayed here is typical of the results of multiple blots using antibodies against GLUT1. In the baseline samples (five subjects, two separate blots for each), 78% of the GLUT1 was in the PM fractions and there was no change in the SEQ ID NO. 10 (GLUT1) distribution (79% in the PM) after insulin infusion.

Figure 13:
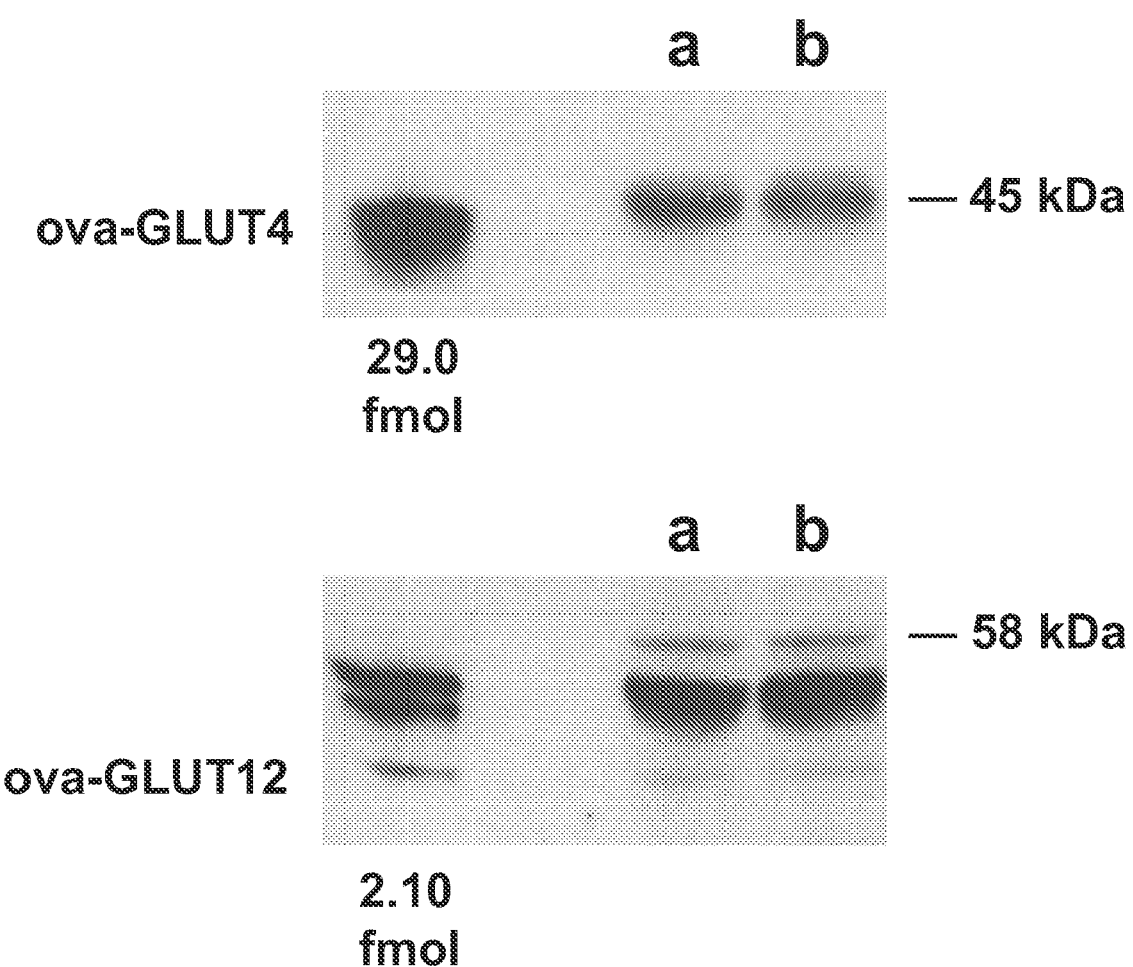
FIG. 13 shows a schematic view of a direct comparison of muscle content of GLUT4 and GLUT12.

FIG. 13. Direct comparison of muscle content of SEQ ID NO. 12 (GLUT4) and SEQ ID NO. 16 (GLUT12). Representative blots for SEQ ID NO. 12 (GLUT4) and SEQ ID NO. 16 (GLUT12) content in homogenates of muscle biopsies obtained from the vastus lateralis from normal volunteers are shown here. In this series of experiments, 10 μg protein from the muscle homogenates was applied to each lane of the gel. Both of the ovaGLUT constructs shown here had mobility consistent with a molecular size of 40 kDa. The SEQ ID NO. 12 (GLUT4) in the muscle samples exhibited a mobility suggesting 45 kDa and the SEQ ID NO. 16 (GLUT12) mobility suggested molecular size of 58 kDa. The SEQ ID NO. 16 (GLUT12) blot contains strong non-specific signals at about 49 kDa. In the presence of the immunization peptide, the bands labeled ova-GLUT12 and 58 kDa were absent but the 49 kDa bands were not diminished. The blots used for these quantifications evaluated biopsies from six subjects and were performed three times each for SEQ ID NO. 12 (GLUT4) and SEQ 11) NO. 16 (GLUM).

Figure 14:
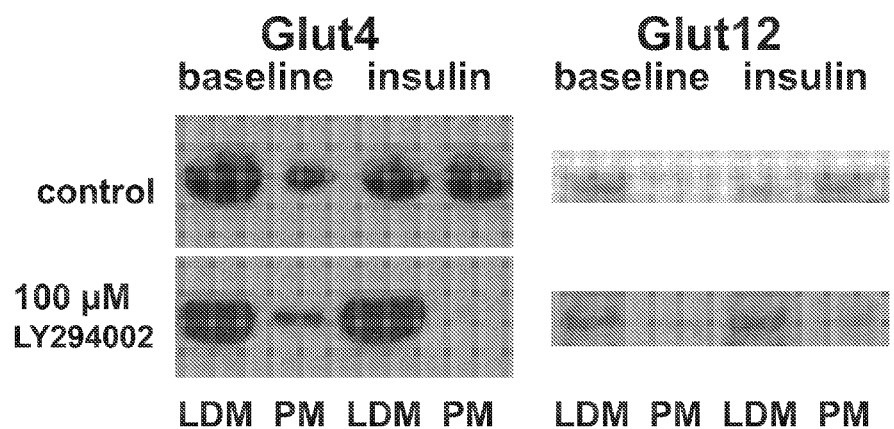
FIG. 14A shows a schematic view of gel measurement results regarding the inhibition of translocation of GLUT4 and GLUT12 in L6 muscle cells in culture.
FIG. 14B shows a schematic graphical view of GLUT4 in PM fraction versus insulin LY294002 concentration.
FIG. 14C shows a schematic graphical view of GLUT12 in PM fraction versus insulin LY294002 concentration.
Figure 14:
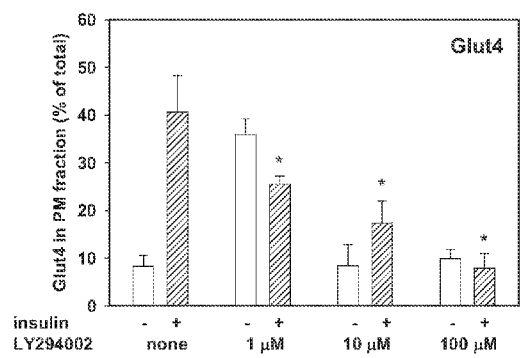
Figure 14:
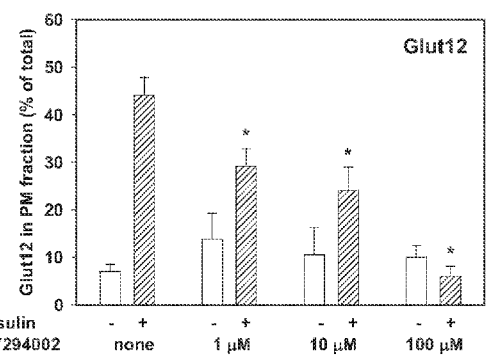

FIG. 14. Inhibition of translocation of SEQ ID NO. 12 (GLUT4) and SEQ ID NO. 16 (GLUT12) in L6 muscle cells in culture: L6 cells were cultured to near confluence in 35 mm dishes and then the growth medium was replaced with medium without serum for one hour. Cells were then incubated at 37° C. for another hour in the presence or absence of insulin (10 ng/mL) with concentrations of the PI3-K inhibitor LY294002 at 0, 1 μM, 10 μM, and 100 μM. After harvesting and fractionating the cells, samples from the fractions were subjected to immunoblotting and digital images were quantified by image analysis software. Panel A shows typical immunoblots and Panels B and C show summary graphs of the quantitative analysis. Portions of both SEQ ID NO. 12 (GLUT4) and SEQ ID NO. 16 (GLUT12) moved from the fraction to the PM fraction in response to incubation with insulin. At 1 μM LY294002 in the absence of insulin, SEQ ID NO. 12 (GLUT4) and SEQ ID NO. 16 (GLUT12) were more in the PM fraction than in the absence of LY294002, suggesting a PI3-K agonist effect at the lowest concentration. The translocation induced by insulin was reduced by the presence of LY294002 in a dose-responsive manner over the full range of concentrations tested.

What is claimed is:

1. A method for making a chimeric protein for use in western blotting, the method comprising the step of amplifying ovalbumin from of SEQ 29 using the primers of SEQ ID NO: 19 (oval F) and of SEQ ID NO: 23 (ova glut4R) and a polymerase from Family A.

2. The method of claim 1 wherein the Family A polymerase comprises T7 DNA polymerase.

3. The method of claim 1 wherein the amplifying step further comprises the step of expressing the chimeric protein using a coupled in vitro transcription/translation system.

4. The method of claim 1 further comprising the step of quantifying the chimeric protein.

5. The method of claim 1 further comprising the step of performing quantitative immunoblots for the protein SEQ ID NO:12 using image analysis of blots that include known amounts of the corresponding chimeric protein.

6. The method of claim 5 further comprising the step of quantifying the chimeric protein.

* * * * *

SEQUENCE LISTING

<160> NUMBER OF SEQ ID NOS: 28

<210> SEQ ID NO 1
<211> LENGTH: 1185
<212> TYPE: DNA
<213> ORGANISM: human

<400> SEQUENCE: 1

| | | | | | |
|---|---|---|---|---|---|
| atggcagcaa | gcatggaatt | ttgttttgat | gtattcaagg | agctcaaagt | ccaccatgcc | 60 |
| aatgagaaca | tcttctactg | ccccattgcc | atcatgtcag | ctctagccat | ggtatacctg | 120 |
| ggtgcaaaag | acagcaccag | gacacagata | aataaggttg | ttcgctttga | taaacttcca | 180 |
| ggattcggag | acagtattga | agctcagtgt | ggcacatctg | taaacgttca | ctcttcactt | 240 |
| agagacatcc | tcaaccaaat | caccaaacca | aatgatgttt | attcgttcag | ccttgccagt | 300 |
| agactttatg | ctgaagagag | atacccaatc | ctgccagaat | acttgcagtg | tgtgaaggaa | 360 |
| ctgtatagag | gaggcttgga | acctatcaac | tttcaaacag | ctgcagatca | agccagagag | 420 |
| ctcatcaatt | cctgggtaga | aagtcagaca | aatggaatta | tcagaaatgt | ccttcagcca | 480 |
| agctccgtgg | attctcaaac | tgcaatggtt | ctggttaatg | ccattgtctt | caaaggactg | 540 |
| tgggagaaaa | catttaagga | tgaagacaca | caagcaatgc | ctttcagagt | gactgagcaa | 600 |
| gaaagcaaac | ctgtgcagat | gatgtaccag | attggtttat | ttagagtggc | atcaatggct | 660 |
| tctgagaaaa | tgaagatcct | ggagcttcca | tttgccagtg | ggacaatgag | catgttggtg | 720 |
| ctgttgcctg | atgaagtctc | aggccttgag | cagcttgaga | gtataatcaa | cttttgaaaaa | 780 |
| ctgactgaat | ggaccagttc | taatgttatg | gaagagagga | agatcaaagt | gtacttacct | 840 |
| cgcatgaaga | tggaggaaaa | atacaacctc | acatctgtct | taatggctat | gggcattact | 900 |
| gacgtgttta | gctcttcagc | caatctgtct | ggcatctcct | cagcagagag | cctgaagata | 960 |
| tctcaagctg | tccatgcagc | acatgcagaa | atcaatgaag | caggcagaga | ggtggtaggg | 1020 |
| tcagcagagg | ctggagtgga | tgctgcaagc | gtctctgaag | aatttagggc | tgaccatcca | 1080 |
| ttcctcttct | gtatcaagca | catcgcaacc | aacgccgttc | tcttctttgg | cagatgtgtt | 1140 |
| tcccctgagc | tgttccatcc | actgggcgct | gattctcaag | tgtaa | | 1185 |

<210> SEQ ID NO 2
<211> LENGTH: 1185
<212> TYPE: DNA
<213> ORGANISM: human

<400> SEQUENCE: 2

| | | | | | |
|---|---|---|---|---|---|
| atggcagcaa | gcatggaatt | ttgttttgat | gtattcaagg | agctcaaagt | ccaccatgcc | 60 |
| aatgagaaca | tcttctactg | ccccattgcc | atcatgtcag | ctctagccat | ggtatacctg | 120 |
| ggtgcaaaag | acagcaccag | gacacagata | aataaggttg | ttcgctttga | taaacttcca | 180 |
| ggattcggag | acagtattga | agctcagtgt | ggcacatctg | taaacgttca | ctcttcactt | 240 |
| agagacatcc | tcaaccaaat | caccaaacca | aatgatgttt | attcgttcag | ccttgccagt | 300 |
| agactttatg | ctgaagagag | atacccaatc | ctgccagaat | acttgcagtg | tgtgaaggaa | 360 |
| ctgtatagag | gaggcttgga | acctatcaac | tttcaaacag | ctgcagatca | agccagagag | 420 |
| ctcatcaatt | cctgggtaga | aagtcagaca | aatggaatta | tcagaaatgt | ccttcagcca | 480 |
| agctccgtgg | attctcaaac | tgcaatggtt | ctggttaatg | ccattgtctt | caaaggactg | 540 |
| tgggagaaaa | catttaagga | tgaagacaca | caagcaatgc | ctttcagagt | gactgagcaa | 600 |

```
gaaagcaaac ctgtgcagat gatgtaccag attggtttat ttagagtggc atcaatggct      660
tctgagaaaa tgaagatcct ggagcttcca tttgccagtg ggacaatgag catgttggtg      720
ctgttgcctg atgaagtctc aggccttgag cagcttgaga gtataatcaa ctttgaaaaa      780
ctgactgaat ggaccagttc taatgttatg aagagagga agatcaaagt gtacttacct      840
cgcatgaaga tggaggaaaa atacaacctc acatctgtct taatggctat gggcattact      900
gacgtgttta gctcttcagc caatctgtct ggcatctcct cagcagagag cctgaagata      960
tctcaagctg tccatgcagc acatgcagaa atcaatgaag caggcagaga ggtggtaggg     1020
tcagcagagg ctggagtgga tgctgcaagc gtctctgaag aatttagggc tgaccatcca     1080
ttcctcttct gtatcaagca catcgcaacc aacgccgttc tcttctttgg cagatgtgtt     1140
tccccttcta tcgagcctgc taaggagacc accaccaatg tctaa                    1185

<210> SEQ ID NO 3
<211> LENGTH: 1185
<212> TYPE: DNA
<213> ORGANISM: human

<400> SEQUENCE: 3
atggcagcaa gcatggaatt ttgttttgat gtattcaagg agctcaaagt ccaccatgcc       60
aatgagaaca tcttctactg ccccattgcc atcatgtcag ctctagccat ggtatacctg      120
ggtgcaaaag acagcaccag gacacagata ataaggttg ttcgctttga taaacttcca      180 ggatcggag acagtattga agctcagtgt ggcacatctg taaacgttca ctcttcactt      240
agagacatcc tcaaccaaat caccaaacca atgatgtttt attcgttcag ccttgccagt      300
agactttatg ctgaagagag atacccaatc ctgccagaat acttgcagtg tgtgaaggaa      360
ctgtatagag gaggcttgga acctatcaac tttcaaacag ctgcagatca agccagagag      420
ctcatcaatt cctgggtaga aagtcagaca atggaatta tcagaaatgt ccttcagcca      480
agctccgtgg attctcaaac tgcaatggtt ctggttaatg ccattgtctt caaaggactg      540
tgggagaaaa catttaagga tgaagacaca caagcaatgc ctttcagagt gactgagcaa      600
gaaagcaaac ctgtgcagat gatgtaccag attggtttat ttagagtggc atcaatggct      660
tctgagaaaa tgaagatcct ggagcttcca tttgccagtg ggacaatgag catgttggtg      720
ctgttgcctg atgaagtctc aggccttgag cagcttgaga gtataatcaa ctttgaaaaa      780
ctgactgaat ggaccagttc taatgttatg aagagagga agatcaaagt gtacttacct      840
cgcatgaaga tggaggaaaa atacaacctc acatctgtct taatggctat gggcattact      900
gacgtgttta gctcttcagc caatctgtct ggcatctcct cagcagagag cctgaagata      960
tctcaagctg tccatgcagc acatgcagaa atcaatgaag caggcagaga ggtggtaggg     1020
tcagcagagg ctggagtgga tgctgcaagc gtctctgaag aatttagggc tgaccatcca     1080
ttcctcttct gtatcaagca catcgcaacc aacgccgttc tcttctttgg cagatgtgtt     1140 tccccctaccg aacttgaata tttaggcccg gatgagaacg attga                    1185

<210> SEQ ID NO 4
<211> LENGTH: 1185
<212> TYPE: DNA
<213> ORGANISM: human

<400> SEQUENCE: 4
atggcagcaa gcatggaatt ttgttttgat gtattcaagg agctcaaagt ccaccatgcc       60
aatgagaaca tcttctactg ccccattgcc atcatgtcag ctctagccat ggtatacctg      120
```

-continued

```
ggtgcaaaag acagcaccag gacacagata aataaggttg ttcgctttga taaacttcca      180
ggattcggag acagtattga agctcagtgt ggcacatctg taaacgttca ctcttcactt      240
agagacatcc tcaaccaaat caccaaacca aatgatgttt attcgttcag ccttgccagt      300
agactttatg ctgaagagag atacccaatc ctgccagaat acttgcagtg tgtgaaggaa      360
ctgtatagag gaggcttgga acctatcaac tttcaaacag ctgcagatca agccagagag      420
ctcatcaatt cctgggtaga aagtcagaca aatggaatta tcagaaatgt ccttcagcca      480
agctccgtgg attctcaaac tgcaatggtt ctggttaatg ccattgtctt caaaggactg      540
tgggagaaaa catttaagga tgaagacaca caagcaatgc ctttcagagt gactgagcaa      600
gaaagcaaac ctgtgcagat gatgtaccag attggtttat ttagagtggc atcaatggct      660
tctgagaaaa tgaagatcct ggagcttcca tttgccagtg ggacaatgag catgttggtg      720
ctgttgcctg atgaagtctc aggccttgag cagcttgaga gtataatcaa ctttgaaaaa      780
ctgactgaat ggaccagttc taatgttatg gaagagagga agatcaaagt gtacttacct      840
cgcatgaaga tggaggaaaa atacaacctc acatctgtct taatggctat gggcattact      900
gacgtgttta gctcttcagc caatctgtct ggcatctcct cagcagagag cctgaagata      960
tctcaagctg tccatgcagc acatgcagaa atcaatgaag caggcagaga ggtggtaggg     1020
tcagcagagg ctggagtgga tgctgcaagc gtctctgaag aatttagggc tgaccatcca     1080
ttcctcttct gtatcaagca catcgcaacc aacgccgttc tcttctttgg cagatgtgtt     1140
tcccctgaac tgaaagagct tccacctgtc acttcagagc agtaa                     1185
```

<210> SEQ ID NO 5
<211> LENGTH: 1185
<212> TYPE: DNA
<213> ORGANISM: human

<400> SEQUENCE: 5

```
atggcagcaa gcatggaatt ttgttttgat gtattcaagg agctcaaagt ccaccatgcc       60
aatgagaaca tcttctactg ccccattgcc atcatgtcag ctctagccat ggtataccctg     120 ggtgcaaaag acagcaccag gacacagata aataaggttg ttcgctttga taaacttcca      180
ggattcggag acagtattga agctcagtgt ggcacatctg taaacgttca ctcttcactt      240
agagacatcc tcaaccaaat caccaaacca aatgatgttt attcgttcag ccttgccagt      300
agactttatg ctgaagagag atacccaatc ctgccagaat acttgcagtg tgtgaaggaa      360
ctgtatagag gaggcttgga acctatcaac tttcaaacag ctgcagatca agccagagag      420
ctcatcaatt cctgggtaga aagtcagaca aatggaatta tcagaaatgt ccttcagcca      480
agctccgtgg attctcaaac tgcaatggtt ctggttaatg ccattgtctt caaaggactg      540
tgggagaaaa catttaagga tgaagacaca caagcaatgc ctttcagagt gactgagcaa      600
gaaagcaaac ctgtgcagat gatgtaccag attggtttat ttagagtggc atcaatggct      660
tctgagaaaa tgaagatcct ggagcttcca tttgccagtg ggacaatgag catgttggtg      720
ctgttgcctg atgaagtctc aggccttgag cagcttgaga gtataatcaa ctttgaaaaa      780
ctgactgaat ggaccagttc taatgttatg gaagagagga agatcaaagt gtacttacct      840
cgcatgaaga tggaggaaaa atacaacctc acatctgtct taatggctat gggcattact      900
gacgtgttta gctcttcagc caatctgtct ggcatctcct cagcagagag cctgaagata      960
tctcaagctg tccatgcagc acatgcagaa atcaatgaag caggcagaga ggtggtaggg     1020
tcagcagagg ctggagtgga tgctgcaagc gtctctgaag aatttagggc tgaccatcca     1080
```

| ttcctcttct gtatcaagca catcgcaacc aacgccgttc tcttctttgg cagatgtgtt | 1140 |
| tccccttctt tcttccgtat gggccgtcgt tctttcctgc gttaa | 1185 |

<210> SEQ ID NO 6
<211> LENGTH: 1185
<212> TYPE: DNA
<213> ORGANISM: human

<400> SEQUENCE: 6

| atggcagcaa gcatggaatt ttgttttgat gtattcaagg agctcaaagt ccaccatgcc | 60 |
| aatgagaaca tcttctactg ccccattgcc atcatgtcag ctctagccat ggtatacctg | 120 |
| ggtgcaaaag acagcaccag gacacagata aataaggttg ttcgctttga taaacttcca | 180 |
| ggattcggag acagtattga agctcagtgt ggcacatctg taaacgttca ctcttcactt | 240 |
| agagacatcc tcaaccaaat caccaaacca aatgatgttt attcgttcag ccttgccagt | 300 |
| agactttatg ctgaagagag atacccaatc ctgccagaat acttgcagtg tgtgaaggaa | 360 |
| ctgtatagag gaggcttgga acctatcaac tttcaaacag ctgcagatca agccagagag | 420 |
| ctcatcaatt cctgggtaga aagtcagaca aatggaatta tcagaaatgt ccttcagcca | 480 |
| agctccgtgg attctcaaac tgcaatggtt ctggttaatg ccattgtctt caaaggactg | 540 |
| tgggagaaaa catttaagga tgaagacaca caagcaatgc ctttcagagt gactgagcaa | 600 |
| gaaagcaaac ctgtgcagat gatgtaccag attggtttat ttagagtggc atcaatggct | 660 |
| tctgagaaaa tgaagatcct ggagcttcca tttgccagtg ggacaatgag catgttggtg | 720 |
| ctgttgcctg atgaagtctc aggccttgag cagcttgaga gtataatcaa ctttgaaaaa | 780 |
| ctgactgaat ggaccagttc taatgttatg gaagagagga gatcaaaagt gtacttacct | 840 |
| cgcatgaaga tggaggaaaa atacaacctc acatctgtct taatggctat gggcattact | 900 |
| gacgtgttta gctcttcagc caatctgtct ggcatctcct cagcagagag cctgaagata | 960 |
| tctcaagctg tccatgcagc acatgcagaa atcaatgaag caggcagaga ggtggtaggg | 1020 |
| tcagcagagg ctggagtgga tgctgcaagc gtctctgaag aatttagggc tgaccatcca | 1080 |
| ttcctcttct gtatcaagca catcgcaacc aacgccgttc tcttctttgg cagatgtgtt | 1140 |
| tccccctactg tcgaacaaat cacagcacat tttgagggtc gataa | 1185 |

<210> SEQ ID NO 7
<211> LENGTH: 1185
<212> TYPE: DNA
<213> ORGANISM: human

<400> SEQUENCE: 7

| atggcagcaa gcatggaatt ttgttttgat gtattcaagg agctcaaagt ccaccatgcc | 60 |
| aatgagaaca tcttctactg ccccattgcc atcatgtcag ctctagccat ggtatacctg | 120 |
| ggtgcaaaag acagcaccag gacacagata aataaggttg ttcgctttga taaacttcca | 180 |
| ggattcggag acagtattga agctcagtgt ggcacatctg taaacgttca ctcttcactt | 240 |
| agagacatcc tcaaccaaat caccaaacca aatgatgttt attcgttcag ccttgccagt | 300 |
| agactttatg ctgaagagag atacccaatc ctgccagaat acttgcagtg tgtgaaggaa | 360 |
| ctgtatagag gaggcttgga acctatcaac tttcaaacag ctgcagatca agccagagag | 420 |
| ctcatcaatt cctgggtaga aagtcagaca aatggaatta tcagaaatgt ccttcagcca | 480 |
| agctccgtgg attctcaaac tgcaatggtt ctggttaatg ccattgtctt caaaggactg | 540 |
| tgggagaaaa catttaagga tgaagacaca caagcaatgc ctttcagagt gactgagcaa | 600 |

-continued

```
gaaagcaaac ctgtgcagat gatgtaccag attggtttat ttagagtggc atcaatggct     660
tctgagaaaa tgaagatcct ggagcttcca tttgccagtg ggacaatgag catgttggtg     720
ctgttgcctg atgaagtctc aggccttgag cagcttgaga gtataatcaa ctttgaaaaa     780
ctgactgaat ggaccagttc taatgttatg gaagagagga agatcaaagt gtacttacct     840
cgcatgaaga tggaggaaaa atacaacctc acatctgtct taatggctat gggcattact     900
gacgtgttta gctcttcagc caatctgtct ggcatctcct cagcagagag cctgaagata     960
tctcaagctg tccatgcagc acatgcagaa atcaatgaag caggcagaga ggtggtaggg    1020
tcagcagagg ctggagtgga tgctgcaagc gtctctgaag aatttagggc tgaccatcca    1080
ttcctcttct gtatcaagca catcgcaacc aacgccgttc tcttctttgg cagatgtgtt    1140
tcccctggta ggggtcaatc caggcagctt tctccatata cctaa                   1185

<210> SEQ ID NO 8
<211> LENGTH: 1185
<212> TYPE: DNA
<213> ORGANISM: human

<400> SEQUENCE: 8
atggcagcaa gcatggaatt ttgttttgat gtattcaagg agctcaaagt ccaccatgcc      60
aatgagaaca tcttctactg ccccattgcc atcatgtcag ctctagccat ggtatacctg     120
ggtgcaaaag acagcaccag gacacagata aataaggttg ttcgctttga taaacttcca     180
ggattcggag acagtattga agctcagtgt ggcacatctg taaacgttca ctcttcactt     240
agagacatcc tcaaccaaat caccaaaacca atgatgtttt attcgttcag ccttgccagt    300
agactttatg ctgaagagag atacccaatc ctgccagaat acttgcagtg tgtgaaggaa     360
ctgtatagag gaggcttgga acctatcaac tttcaaacag ctgcagatca agccagagag     420
ctcatcaatt cctgggtaga aagtcagaca aatggaatta tcagaaatgt ccttcagcca     480
agctccgtgg attctcaaac tgcaatggtt ctggttaatg ccattgtctt caaaggactg     540
tgggagaaaa catttaagga tgaagacaca caagcaatgc ttttcagagt gactgagcaa     600
gaaagcaaac ctgtgcagat gatgtaccag attggtttat ttagagtggc atcaatggct     660
tctgagaaaa tgaagatcct ggagcttcca tttgccagtg ggacaatgag catgttggtg     720
ctgttgcctg atgaagtctc aggccttgag cagcttgaga gtataatcaa ctttgaaaaa     780
ctgactgaat ggaccagttc taatgttatg gaagagagga agatcaaagt gtacttacct     840
cgcatgaaga tggaggaaaa atacaacctc acatctgtct taatggctat gggcattact     900
gacgtgttta gctcttcagc caatctgtct ggcatctcct cagcagagag cctgaagata     960
tctcaagctg tccatgcagc acatgcagaa atcaatgaag caggcagaga ggtggtaggg    1020
tcagcagagg ctggagtgga tgctgcaagc gtctctgaag aatttagggc tgaccatcca    1080
ttcctcttct gtatcaagca catcgcaacc aacgccgttc tcttctttgg cagatgtgtt    1140
tcccctcgaa tgcagccagt gaaagaacca ccgggtaacg cgtaa                   1185

<210> SEQ ID NO 9
<211> LENGTH: 1212
<212> TYPE: DNA
<213> ORGANISM: human

<400> SEQUENCE: 9
atggcagcaa gcatggaatt ttgttttgat gtattcaagg agctcaaagt ccaccatgcc      60
aatgagaaca tcttctactg ccccattgcc atcatgtcag ctctagccat ggtatacctg     120
```

-continued

```
ggtgcaaaag acagcaccag gacacagata aataaggttg ttcgctttga taaacttcca      180
ggattcggag acagtattga agctcagtgt ggcacatctg taaacgttca ctcttcactt      240
agagacatcc tcaaccaaat caccaaacca aatgatgttt attcgttcag ccttgccagt      300
agactttatg ctgaagagag atacccaatc ctgccagaat acttgcagtg tgtgaaggaa      360
ctgtatagag gaggcttgga acctatcaac tttcaaacag ctgcagatca agccagagag      420
ctcatcaatt cctgggtaga aagtcagaca atggaatta tcagaaatgt ccttcagcca       480
agctccgtgg attctcaaac tgcaatggtt ctggttaatg ccattgtctt caaaggactg      540
tgggagaaaa catttaagga tgaagacaca caagcaatgc ctttcagagt gactgagcaa      600
gaaagcaaac ctgtgcagat gatgtaccag attggtttat ttagagtggc atcaatggct      660
tctgagaaaa tgaagatcct ggagcttcca tttgccagtg ggacaatgag catgttggtg      720
ctgttgcctg atgaagtctc aggccttgag cagcttgaga gtataatcaa ctttgaaaaa      780
ctgactgaat ggaccagttc taatgttatg gaagagagga agatcaaagt gtacttacct      840
cgcatgaaga tggaggaaaa atacaacctc acatctgtct taatggctat gggcattact      900
gacgtgttta gctcttcagc caatctgtct ggcatctcct cagcagagag cctgaagata      960
tctcaagctg tccatgcagc acatgcagaa atcaatgaag caggcagaga ggtggtaggg     1020
tcagcagagg ctggagtgga tgctgcaagc gtctctgaag aatttagggc tgaccatcca     1080
ttcctcttct gtatcaagca catcgcaacc aacgccgttc tcttctttgg cagatgtgtt     1140
tcccctagca ccctgttcac catggatatc tacgccaaag tccgcaaaag agcatctgag     1200
aaagagctgt aa                                                         1212
```

<210> SEQ ID NO 10  
<211> LENGTH: 394  
<212> TYPE: PRT  
<213> ORGANISM: human

<400> SEQUENCE: 10

```
Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                20                  25                  30

Ser Ala Leu Ala Met Val Tyr Leu Gly Ala Lys Asp Ser Thr Arg Thr
            35                  40                  45

Gln Ile Asn Lys Val Val Arg Phe Asp Lys Leu Pro Gly Phe Gly Asp
        50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
                85                  90                  95

Ser Leu Ala Ser Arg Leu Tyr Ala Glu Glu Arg Tyr Pro Ile Leu Pro
            100                 105                 110

Glu Tyr Leu Gln Cys Val Lys Glu Leu Tyr Arg Gly Gly Leu Glu Pro
        115                 120                 125

Ile Asn Phe Gln Thr Ala Ala Asp Gln Ala Arg Glu Leu Ile Asn Ser
    130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
```

```
                    180                 185                 190
Met Pro Phe Arg Val Thr Glu Gln Glu Ser Lys Pro Val Gln Met Met
                195                 200                 205

Tyr Gln Ile Gly Leu Phe Arg Val Ala Ser Met Ala Ser Glu Lys Met
            210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
        275                 280                 285

Asn Leu Thr Ser Val Leu Met Ala Met Gly Ile Thr Asp Val Phe Ser
        290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
            355                 360                 365

Ala Thr Asn Ala Val Leu Phe Phe Gly Arg Cys Val Ser Pro Glu Leu
        370                 375                 380

Phe His Pro Leu Gly Ala Asp Ser Gln Val
385                 390

<210> SEQ ID NO 11
<211> LENGTH: 394
<212> TYPE: PRT
<213> ORGANISM: human

<400> SEQUENCE: 11

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
            20                  25                  30

Ser Ala Leu Ala Met Val Tyr Leu Gly Ala Lys Asp Ser Thr Arg Thr
        35                  40                  45

Gln Ile Asn Lys Val Val Arg Phe Asp Lys Leu Pro Gly Phe Gly Asp
    50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
                85                  90                  95

Ser Leu Ala Ser Arg Leu Tyr Ala Glu Glu Arg Tyr Pro Ile Leu Pro
            100                 105                 110

Glu Tyr Leu Gln Cys Val Lys Glu Leu Tyr Arg Gly Gly Leu Glu Pro
        115                 120                 125

Ile Asn Phe Gln Thr Ala Ala Asp Gln Ala Arg Glu Leu Ile Asn Ser
    130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
```

```
                165                 170                 175
Phe Lys Gly Leu Trp Glu Lys Thr Phe Lys Asp Glu Asp Thr Gln Ala
            180                 185                 190
Met Pro Phe Arg Val Thr Glu Gln Glu Ser Lys Pro Val Gln Met Met
            195                 200                 205
Tyr Gln Ile Gly Leu Phe Arg Val Ala Ser Met Ala Ser Glu Lys Met
            210                 215                 220
Lys Ile Leu Glu Leu Pro Phe Ala Ser Gly Thr Met Ser Met Leu Val
225                 230                 235                 240
Leu Leu Pro Asp Glu Val Ser Gly Leu Glu Gln Leu Glu Ser Ile Ile
                245                 250                 255
Asn Phe Glu Lys Leu Thr Glu Trp Thr Ser Ser Asn Val Met Glu Glu
            260                 265                 270
Arg Lys Ile Lys Val Tyr Leu Pro Arg Met Lys Met Glu Glu Lys Tyr
            275                 280                 285
Asn Leu Thr Ser Val Leu Met Ala Met Gly Ile Thr Asp Val Phe Ser
            290                 295                 300
Ser Ser Ala Asn Leu Ser Gly Ile Ser Ser Ala Glu Ser Leu Lys Ile
305                 310                 315                 320
Ser Gln Ala Val His Ala Ala His Ala Glu Ile Asn Glu Ala Gly Arg
                325                 330                 335
Glu Val Val Gly Ser Ala Glu Ala Gly Val Asp Ala Ala Ser Val Ser
            340                 345                 350
Glu Glu Phe Arg Ala Asp His Pro Phe Leu Phe Cys Ile Lys His Ile
            355                 360                 365
Ala Thr Asn Ala Val Leu Phe Phe Gly Arg Cys Val Ser Pro Ser Ile
            370                 375                 380
Glu Pro Ala Lys Glu Thr Thr Thr Asn Val
385                 390

<210> SEQ ID NO 12
<211> LENGTH: 394
<212> TYPE: PRT
<213> ORGANISM: human

<400> SEQUENCE: 12

Met Ala Ala Ser Met Glu Phe Cys Phe Asp Val Phe Lys Glu Leu Lys
1               5                   10                  15
Val His His Ala Asn Glu Asn Ile Phe Tyr Cys Pro Ile Ala Ile Met
                20                  25                  30
Ser Ala Leu Ala Met Val Tyr Leu Gly Ala Lys Asp Ser Thr Arg Thr
            35                  40                  45
Gln Ile Asn Lys Val Val Arg Phe Asp Lys Leu Pro Gly Phe Gly Asp
        50                  55                  60
Ser Ile Glu Ala Gln Cys Gly Thr Ser Val Asn Val His Ser Ser Leu
65                  70                  75                  80
Arg Asp Ile Leu Asn Gln Ile Thr Lys Pro Asn Asp Val Tyr Ser Phe
                85                  90                  95
Ser Leu Ala Ser Arg Leu Tyr Ala Glu Glu Arg Tyr Pro Ile Leu Pro
            100                 105                 110
Glu Tyr Leu Gln Cys Val Lys Glu Leu Tyr Arg Gly Gly Leu Glu Pro
            115                 120                 125
Ile Asn Phe Gln Thr Ala Ala Asp Gln Ala Arg Glu Leu Ile Asn Ser
            130                 135                 140
Trp Val Glu Ser Gln Thr Asn Gly Ile Ile Arg Asn Val Leu Gln Pro
```

```
                145                 150                 155                 160
Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
                180                 185                 190

Met Pro Phe Arg Val Thr Glu Gln Glu Ser Lys Pro Val Gln Met Met
                195                 200                 205

Tyr Gln Ile Gly Leu Phe Arg Val Ala Ser Met Ala Ser Glu Lys Met
                210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
                260                 265                 270

Arg Lys Ile Lys Val Tyr Leu Pro Arg Met Lys Met Glu Glu Lys Tyr
                275                 280                 285

Asn Leu Thr Ser Val Leu Met Ala Met Gly Ile Thr Asp Val Phe Ser
                290                 295                 300

Ser Ser Ala Asn Leu Ser Gly Ile Ser Ser Ala Glu Ser Leu Lys Ile
305                 310                 315                 320

Ser Gln Ala Val His Ala His Ala Glu Ile Asn Glu Ala Gly Arg
                325                 330                 335

Glu Val Val Gly Ser Ala Glu Ala Gly Val Asp Ala Ala Ser Val Ser
                340                 345                 350

Glu Glu Phe Arg Ala Asp His Pro Phe Leu Phe Cys Ile Lys His Ile
                355                 360                 365

Ala Thr Asn Ala Val Leu Phe Phe Gly Arg Cys Val Ser Pro Thr Glu
                370                 375                 380

Leu Glu Tyr Leu Gly Pro Asp Glu Asn Asp
385                 390

<210> SEQ ID NO 13
<211> LENGTH: 394
<212> TYPE: PRT
<213> ORGANISM: human

<400> SEQUENCE: 13

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                20                  25                  30

Ser Ala Leu Ala Met Val Tyr Leu Gly Ala Lys Asp Ser Thr Arg Thr
                35                  40                  45

Gln Ile Asn Lys Val Val Arg Phe Asp Lys Leu Pro Gly Phe Gly Asp
                50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
                85                  90                  95

Ser Leu Ala Ser Arg Leu Tyr Ala Glu Glu Arg Tyr Pro Ile Leu Pro
                100                 105                 110

Glu Tyr Leu Gln Cys Val Lys Glu Leu Tyr Arg Gly Gly Leu Glu Pro
                115                 120                 125

Ile Asn Phe Gln Thr Ala Ala Asp Gln Ala Arg Glu Leu Ile Asn Ser
```

```
                        130                 135                 140
Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
            180                 185                 190

Met Pro Phe Arg Val Thr Glu Gln Glu Ser Lys Pro Val Gln Met Met
        195                 200                 205

Tyr Gln Ile Gly Leu Phe Arg Val Ala Ser Met Ala Ser Glu Lys Met
    210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
        275                 280                 285

Asn Leu Thr Ser Val Leu Met Ala Met Gly Ile Thr Asp Val Phe Ser
    290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
        355                 360                 365

Ala Thr Asn Ala Val Leu Phe Phe Gly Arg Cys Val Ser Pro Glu Leu
    370                 375                 380

Lys Glu Leu Pro Pro Val Thr Ser Glu Gln
385                 390

<210> SEQ ID NO 14
<211> LENGTH: 394
<212> TYPE: PRT
<213> ORGANISM: human

<400> SEQUENCE: 14

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                20                  25                  30

Ser Ala Leu Ala Met Val Tyr Leu Gly Ala Lys Asp Ser Thr Arg Thr
            35                  40                  45

Gln Ile Asn Lys Val Val Arg Phe Asp Lys Leu Pro Gly Phe Gly Asp
        50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
                85                  90                  95

Ser Leu Ala Ser Arg Leu Tyr Ala Glu Glu Arg Tyr Pro Ile Leu Pro
            100                 105                 110

Glu Tyr Leu Gln Cys Val Lys Glu Leu Tyr Arg Gly Gly Leu Glu Pro
```

```
                    115                 120                 125
Ile Asn Phe Gln Thr Ala Ala Asp Gln Ala Arg Glu Leu Ile Asn Ser
            130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
            180                 185                 190

Met Pro Phe Arg Val Thr Glu Gln Glu Ser Lys Pro Val Gln Met Met
        195                 200                 205

Tyr Gln Ile Gly Leu Phe Arg Val Ala Ser Met Ala Ser Glu Lys Met
210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
        275                 280                 285

Asn Leu Thr Ser Val Leu Met Ala Met Gly Ile Thr Asp Val Phe Ser
290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
        355                 360                 365

Ala Thr Asn Ala Val Leu Phe Phe Gly Arg Cys Val Ser Pro Ser Phe
370                 375                 380

Phe Arg Met Gly Arg Arg Ser Phe Leu Arg
385                 390

<210> SEQ ID NO 15
<211> LENGTH: 394
<212> TYPE: PRT
<213> ORGANISM: human

<400> SEQUENCE: 15

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
            20                  25                  30

Ser Ala Leu Ala Met Val Tyr Leu Gly Ala Lys Asp Ser Thr Arg Thr
        35                  40                  45

Gln Ile Asn Lys Val Val Arg Phe Asp Lys Leu Pro Gly Phe Gly Asp
    50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
                85                  90                  95

Ser Leu Ala Ser Arg Leu Tyr Ala Glu Glu Arg Tyr Pro Ile Leu Pro
```

```
                100                 105                 110
Glu Tyr Leu Gln Cys Val Lys Glu Leu Tyr Arg Gly Gly Leu Glu Pro
            115                 120                 125

Ile Asn Phe Gln Thr Ala Ala Asp Gln Ala Arg Glu Leu Ile Asn Ser
            130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
                180                 185                 190

Met Pro Phe Arg Val Thr Glu Gln Glu Ser Lys Pro Val Gln Met Met
            195                 200                 205

Tyr Gln Ile Gly Leu Phe Arg Val Ala Ser Met Ala Ser Glu Lys Met
            210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
            275                 280                 285

Asn Leu Thr Ser Val Leu Met Ala Met Gly Ile Thr Asp Val Phe Ser
            290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
            355                 360                 365

Ala Thr Asn Ala Val Leu Phe Phe Gly Arg Cys Val Ser Pro Thr Val
            370                 375                 380

Glu Gln Ile Thr Ala His Phe Glu Gly Arg
385                 390

<210> SEQ ID NO 16
<211> LENGTH: 394
<212> TYPE: PRT
<213> ORGANISM: human

<400> SEQUENCE: 16

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                20                  25                  30

Ser Ala Leu Ala Met Val Tyr Leu Gly Ala Lys Asp Ser Thr Arg Thr
            35                  40                  45

Gln Ile Asn Lys Val Val Arg Phe Asp Lys Leu Pro Gly Phe Gly Asp
        50                  55                  60

Ser Ile Glu Ala Gln Cys Gly Thr Ser Val Asn Val His Ser Ser Leu
65                  70                  75                  80

Arg Asp Ile Leu Asn Gln Ile Thr Lys Pro Asn Asp Val Tyr Ser Phe
```

```
                       85                  90                  95
Ser Leu Ala Ser Arg Leu Tyr Ala Glu Glu Arg Tyr Pro Ile Leu Pro
            100                 105                 110

Glu Tyr Leu Gln Cys Val Lys Glu Leu Tyr Arg Gly Gly Leu Glu Pro
            115                 120                 125

Ile Asn Phe Gln Thr Ala Ala Asp Gln Ala Arg Glu Leu Ile Asn Ser
            130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                    165                 170                 175

Phe Lys Gly Leu Trp Glu Lys Thr Phe Lys Asp Glu Asp Thr Gln Ala
                    180                 185                 190

Met Pro Phe Arg Val Thr Glu Gln Glu Ser Lys Pro Val Gln Met Met
            195                 200                 205

Tyr Gln Ile Gly Leu Phe Arg Val Ala Ser Met Ala Ser Glu Lys Met
            210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                    245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
            275                 280                 285

Asn Leu Thr Ser Val Leu Met Ala Met Gly Ile Thr Asp Val Phe Ser
            290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                    325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
            355                 360                 365

Ala Thr Asn Ala Val Leu Phe Phe Gly Arg Cys Val Ser Pro Gly Arg
            370                 375                 380

Gly Gln Ser Arg Gln Leu Ser Pro Tyr Thr
385                 390

<210> SEQ ID NO 17
<211> LENGTH: 394
<212> TYPE: PRT
<213> ORGANISM: human

<400> SEQUENCE: 17

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                20                  25                  30

Ser Ala Leu Ala Met Val Tyr Leu Gly Ala Lys Asp Ser Thr Arg Thr
            35                  40                  45

Gln Ile Asn Lys Val Val Arg Phe Asp Lys Leu Pro Gly Phe Gly Asp
        50                  55                  60

Ser Ile Glu Ala Gln Cys Gly Thr Ser Val Asn Val His Ser Ser Leu
```

```
                65                  70                  75                  80
Arg Asp Ile Leu Asn Gln Ile Thr Lys Pro Asn Asp Val Tyr Ser Phe
                    85                  90                  95

Ser Leu Ala Ser Arg Leu Tyr Ala Glu Glu Arg Tyr Pro Ile Leu Pro
                    100                 105                 110

Glu Tyr Leu Gln Cys Val Lys Glu Leu Tyr Arg Gly Gly Leu Glu Pro
                    115                 120                 125

Ile Asn Phe Gln Thr Ala Ala Asp Gln Ala Arg Glu Leu Ile Asn Ser
                    130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                    165                 170                 175

Phe Lys Gly Leu Trp Glu Lys Thr Phe Lys Asp Glu Asp Thr Gln Ala
                    180                 185                 190

Met Pro Phe Arg Val Thr Glu Gln Glu Ser Lys Pro Val Gln Met Met
                    195                 200                 205

Tyr Gln Ile Gly Leu Phe Arg Val Ala Ser Met Ala Ser Glu Lys Met
                    210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                    245                 250                 255

Asn Phe Glu Lys Leu Thr Glu Trp Thr Ser Ser Asn Val Met Glu Glu
                    260                 265                 270

Arg Lys Ile Lys Val Tyr Leu Pro Arg Met Lys Met Glu Glu Lys Tyr
                    275                 280                 285

Asn Leu Thr Ser Val Leu Met Ala Met Gly Ile Thr Asp Val Phe Ser
                    290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                    325                 330                 335

Glu Val Val Gly Ser Ala Glu Ala Gly Val Asp Ala Ala Ser Val Ser
                    340                 345                 350

Glu Glu Phe Arg Ala Asp His Pro Phe Leu Phe Cys Ile Lys His Ile
                    355                 360                 365

Ala Thr Asn Ala Val Leu Phe Phe Gly Arg Cys Val Ser Pro Arg Met
                    370                 375                 380

Gln Pro Val Lys Glu Pro Pro Gly Asn Ala
385                 390

<210> SEQ ID NO 18
<211> LENGTH: 403
<212> TYPE: PRT
<213> ORGANISM: human

<400> SEQUENCE: 18

Met Ala Ala Ser Met Glu Phe Cys Phe Asp Val Phe Lys Glu Leu Lys
1               5                   10                  15

Val His His Ala Asn Glu Asn Ile Phe Tyr Cys Pro Ile Ala Ile Met
                    20                  25                  30

Ser Ala Leu Ala Met Val Tyr Leu Gly Ala Lys Asp Ser Thr Arg Thr
                    35                  40                  45

Gln Ile Asn Lys Val Val Arg Phe Asp Lys Leu Pro Gly Phe Gly Asp
```

```
              50                  55                  60
Ser Ile Glu Ala Gln Cys Gly Thr Ser Val Asn Val His Ser Ser Leu
 65                  70                  75                  80

Arg Asp Ile Leu Asn Gln Ile Thr Lys Pro Asn Asp Val Tyr Ser Phe
                 85                  90                  95

Ser Leu Ala Ser Arg Leu Tyr Ala Glu Glu Arg Tyr Pro Ile Leu Pro
            100                 105                 110

Glu Tyr Leu Gln Cys Val Lys Glu Leu Tyr Arg Gly Gly Leu Glu Pro
        115                 120                 125

Ile Asn Phe Gln Thr Ala Ala Asp Gln Ala Arg Glu Leu Ile Asn Ser
    130                 135                 140

Trp Val Glu Ser Gln Thr Asn Gly Ile Ile Arg Asn Val Leu Gln Pro
145                 150                 155                 160

Ser Ser Val Asp Ser Gln Thr Ala Met Val Leu Val Asn Ala Ile Val
                165                 170                 175

Phe Lys Gly Leu Trp Glu Lys Thr Phe Lys Asp Glu Asp Thr Gln Ala
            180                 185                 190

Met Pro Phe Arg Val Thr Glu Gln Glu Ser Lys Pro Val Gln Met Met
        195                 200                 205

Tyr Gln Ile Gly Leu Phe Arg Val Ala Ser Met Ala Ser Glu Lys Met
    210                 215                 220

Lys Ile Leu Glu Leu Pro Phe Ala Ser Gly Thr Met Ser Met Leu Val
225                 230                 235                 240

Leu Leu Pro Asp Glu Val Ser Gly Leu Glu Gln Leu Glu Ser Ile Ile
                245                 250                 255

Asn Phe Glu Lys Leu Thr Glu Trp Thr Ser Ser Asn Val Met Glu Glu
            260                 265                 270

Arg Lys Ile Lys Val Tyr Leu Pro Arg Met Lys Met Glu Glu Lys Tyr
        275                 280                 285

Asn Leu Thr Ser Val Leu Met Ala Met Gly Ile Thr Asp Val Phe Ser
    290                 295                 300

Ser Ser Ala Asn Leu Ser Gly Ile Ser Ser Ala Glu Ser Leu Lys Ile
305                 310                 315                 320

Ser Gln Ala Val His Ala Ala His Ala Glu Ile Asn Glu Ala Gly Arg
                325                 330                 335

Glu Val Val Gly Ser Ala Glu Ala Gly Val Asp Ala Ala Ser Val Ser
            340                 345                 350

Glu Glu Phe Arg Ala Asp His Pro Phe Leu Phe Cys Ile Lys His Ile
        355                 360                 365

Ala Thr Asn Ala Val Leu Phe Phe Gly Arg Cys Val Ser Pro Ser Thr
    370                 375                 380

Leu Phe Thr Met Asp Ile Tyr Ala Lys Val Arg Lys Arg Ala Ser Glu
385                 390                 395                 400

Lys Glu Leu

<210> SEQ ID NO 19
<211> LENGTH: 57
<212> TYPE: DNA
<213> ORGANISM: human

<400> SEQUENCE: 19
attacgactc actataggga gaggaggtat atacatggca gcaagcatgg aattttg        57

<210> SEQ ID NO 20
<211> LENGTH: 61
```

```
<212> TYPE: DNA
<213> ORGANISM: human

<400> SEQUENCE: 20
ttacacttga gaatcagcgc ccagtggatg gaacagctca ggggaaacac atctgccaaa    60
g                                                                   61

<210> SEQ ID NO 21
<211> LENGTH: 61
<212> TYPE: DNA
<213> ORGANISM: human

<400> SEQUENCE: 21
ttagacattg gtggtggtct ccttagcagg ctcgatagaa ggggaaacac atctgccaaa    60
g                                                                   61

<210> SEQ ID NO 22
<211> LENGTH: 61
<212> TYPE: DNA
<213> ORGANISM: human

<400> SEQUENCE: 22
ttacgcgtta cccggggttt ctttcactgg ctgcatgcta ggggaaacac atctgccaaa    60
g                                                                   61

<210> SEQ ID NO 23
<211> LENGTH: 61
<212> TYPE: DNA
<213> ORGANISM: human

<400> SEQUENCE: 23
tcaatcgttc tcatccgggc ctaaatattc aagttcggta ggggaaacac atctgccaaa    60
g                                                                   61

<210> SEQ ID NO 24
<211> LENGTH: 61
<212> TYPE: DNA
<213> ORGANISM: human

<400> SEQUENCE: 24
ttactgctct gaagtgacag gtggaagctc tttcagttca ggggaaacac atctgccaaa    60
g                                                                   61

<210> SEQ ID NO 25
<211> LENGTH: 61
<212> TYPE: DNA
<213> ORGANISM: human

<400> SEQUENCE: 25
ttaacgcagg aaagaacgac ggcccatacg gaagaaagaa ggggaaacac atctgccaaa    60
g                                                                   61

<210> SEQ ID NO 26
<211> LENGTH: 61
<212> TYPE: DNA
<213> ORGANISM: human

<400> SEQUENCE: 26
ttatcgaccc tcaaaatgtg ctgtgatttg ttccagagta ggggaaacac atctgccaaa    60
g                                                                   61
```

<210> SEQ ID NO 27
<211> LENGTH: 61
<212> TYPE: DNA
<213> ORGANISM: human

<400> SEQUENCE: 27
ttaggtctct ggagaaagct gcctggattg acccctacca ggggaaacac atctgccaaa    60
g                                                                    61

<210> SEQ ID NO 28
<211> LENGTH: 88
<212> TYPE: DNA
<213> ORGANISM: human

<400> SEQUENCE: 28
ttacagctct ttctcagatg ctcttttgcg gactttggcg tagatatcca tggtgaacag    60
ggtgctaggg gaaacacatc tgccaaag                                       88